United States Patent
Chae et al.

(10) Patent No.: US 7,291,601 B1
(45) Date of Patent: Nov. 6, 2007

(54) ARGININE-RICH ANTI-VASCULAR ENDOTHELIAL GROWTH FACTOR PEPTIDES THAT INHIBIT GROWTH AND METASTASIS OF HUMAN TUMOR CELLS BY BLOCKING ANGIOGENESIS

(75) Inventors: Chi Bom Chae, Kyungsangbuk do (KR); Dong Goo Bae, Kyungsangbuk-do (KR); Wan Hee Yoon, Taejon (KR)

(73) Assignees: Korea Greencross Corp., Kyunggi-Do (KR); Postech Foundation, Kyungsangbuk-Do (KR)

( * ) Notice: Subject to any disclaimer, the term of this patent is extended or adjusted under 35 U.S.C. 154(b) by 0 days.

(21) Appl. No.: 09/913,956

(22) PCT Filed: Dec. 21, 1999

(86) PCT No.: PCT/KR99/00796

§ 371 (c)(1),
(2), (4) Date: Sep. 13, 2001

(87) PCT Pub. No.: WO01/66127

PCT Pub. Date: Sep. 13, 2001

(51) Int. Cl.
*A61K 38/08* (2006.01)
*C07K 7/06* (2006.01)
(52) U.S. Cl. .................................. 514/17; 530/329
(58) Field of Classification Search .................... None
See application file for complete search history.

(56) References Cited

FOREIGN PATENT DOCUMENTS

| DE | 19724793 A1 | 12/1998 |
| HU | 9702554 A2 * | 11/1999 |
| WO | WO 00/74701 A2 | 12/2000 |

OTHER PUBLICATIONS

Kim et al. Inhibition of vascular endothelial growth factor-induced angiogenesis . . . Nature. Apr. 29, 1993, vol. 362, pp. 841-844.*
Borgstrom et al. Complete inhibition of angiogenesis . . . Cancer Research. Sep. 1996, vol. 56, pp. 4032-4039.*
Ferrer-Montiel et al. Selected peptides targeted to the NMDA receptor channel . . . Nature Biotechnology. Mar. 1998, vol. 16, pp. 286-291.*
Iida et al. Macrophage Activation And Host Augmentation . . . International Journal of Immunopharmacology. 1989, vol. 11, No. 3, pp. 249-258.*
Bae D G et al: "Arginine-rich anti-vascular endothelial growth factor peptides inhibit tumor growth and metastasis by blocking angiogenesis"; The Journal of Biological Chemistry; United States May 5, 2000; vol. 275, No. 18, pp. 13588-13596.
Supplementary Partial European Search Report, dated Jan. 27, 2004, Examiner O. Lechner.

* cited by examiner

Primary Examiner—Jeffrey Edwin Russel
(74) Attorney, Agent, or Firm—Staas & Halsey LLP

(57) ABSTRACT

Disclosed are novel peptides inhibitory of the activity of vascular endothelial growth factor (VEGF) and their use in the treatment of angiogenesis-related diseases, including cancer. A combinatorial library of peptides consisting of six amino acid residues were chemically synthesize and, from the library, specific amino acid residues for each amino acid position were screened by comparing their inhibitory activity against VEGF binding to the cell surface receptor. The novel peptide sequences thus obtained bind to VEGF and block the binding of VEGF to its receptors present on the surface of vascular endothelial cells, thereby inhibiting the hormonal activity of VEGF. The peptides inhibit the angiogenesis induced by VEGF and human cancer cells. Also, the peptides inhibit growth and metastasis of human cancer cells transplanted to mice. Thus, the peptides can be used to treat angiogenesis-related diseases, including cancer, diabetic retinopathy, rheumatoid arthritis, etc.

4 Claims, 20 Drawing Sheets

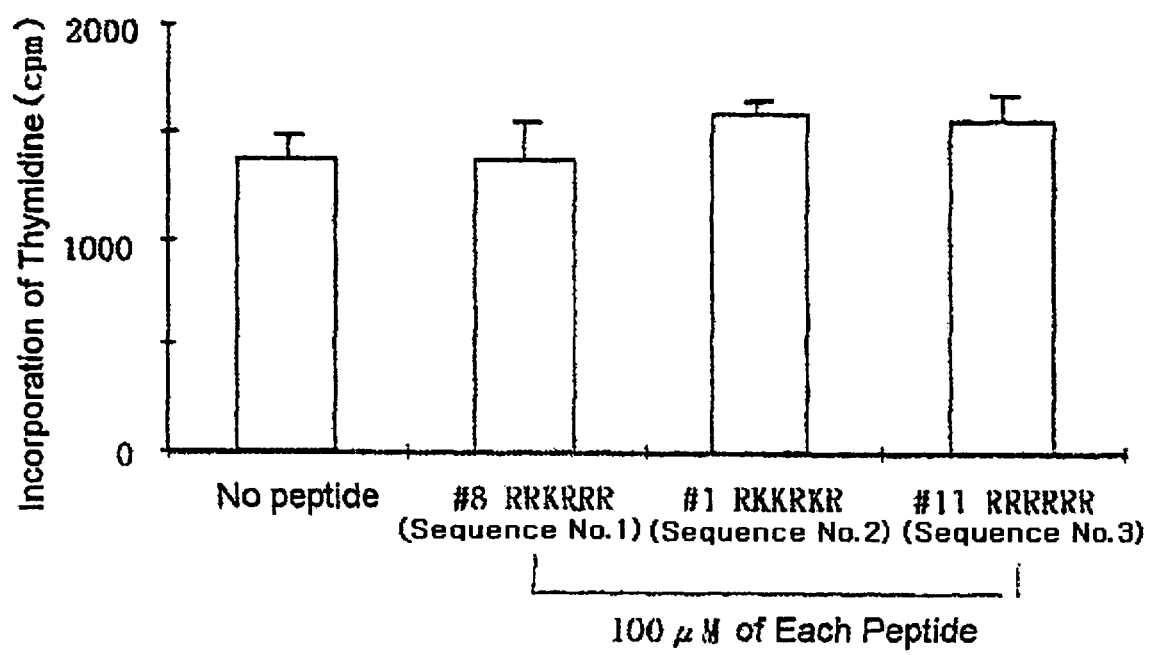

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial sequence
<220> FEATURE:
<223> OTHER INFORMATION: Peptide

<400> SEQUENCE: 1

Arg Arg Lys Arg Arg Arg
1               5

<210> SEQ ID NO 2
<211> LENGTH: 6
<212> TYPE: PRT
<213> ORGANISM: Artificial sequence
<220> FEATURE:
<223> OTHER INFORMATION: Peptide

<400> SEQUENCE: 2

Arg Lys Lys Arg Lys Arg
1               5

<210> SEQ ID NO 3
<211> LENGTH: 6
<212> TYPE: PRT
<213> ORGANISM: Artificial sequence
```

```
<220> FEATURE:
<223> OTHER INFORMATION: Peptide

<400> SEQUENCE: 3

Arg Arg Arg Arg Arg Arg
1               5

<210> SEQ ID NO 4
<211> LENGTH: 6
<212> TYPE: PRT
<213> ORGANISM: Artificial sequence
<220> FEATURE:
<223> OTHER INFORMATION: Peptide

<400> SEQUENCE: 4

Lys Lys Lys Lys Lys Lys
1               5

<210> SEQ ID NO 5
<211> LENGTH: 6
<212> TYPE: PRT
<213> ORGANISM: Artificial sequence
<220> FEATURE:
<223> OTHER INFORMATION: Peptide

<400> SEQUENCE: 5

Glu Glu Phe Asp Asp Ala
1               5
```

ARGININE-RICH ANTI-VASCULAR ENDOTHELIAL GROWTH FACTOR PEPTIDES THAT INHIBIT GROWTH AND METASTASIS OF HUMAN TUMOR CELLS BY BLOCKING ANGIOGENESIS

FIELD OF THE INVENTION

The present invention relates to a novel peptide that shows inhibitory activity of the vascular endothelial growth factor (hereinafter, referred to as "VEGF"), which is an angiogenic factor, and the use thereof for the prophylaxis and treatment of cancers and angiogenesis-related diseases.

BACKGROUND OF THE INVENTION

With a definition for the generation of new blood vessels in adult tissues, but not for the vasculogenesis during embryogenesis or development, angiogenesis is a biological process in which angiogenic factors, substrate molecules and accessory cells are elaborately synchronized in time and space. The generation of blood vessels is achieved in complex, collective, multi-step bioreactions, playing a very important role in normal physiological functions, such as wound healing, embryogenesis, etc. In the body, angiogenesis is conducted at a necessary time in a necessary place for a required period under an elaborate system controlled by the balance between angiogenic factors and antiangiogenic factors (Loitta, L. A. et al., Cell, 64, 327 (1991)).

A failure in controlling the elaborate mechanism of angiogenesis results in various diseases, including cancers, diabetic retinopathy, rheumatoid arthritis, etc (Kohn, E. C. et al., Proc. Natl. Acad. Sci. USA, 92, 1307 (1995); Folkman, J. et al., Science, 235, 442 (1997); Risau, W., Nature, 386, 671 (1997)). Also, angiogenesis is revealed to be indispensable for the growth and metastasis of cancer cells because it enables nutrients to be provided to cancer cells and makes passageways through which cancer cells are transferred to other sites (Hanahan, D. et al., Cell, 86, 353 (1996); Skobe, M. et al., Nature Med., 3, 1222 (1997)). In detail, cancerous cells grow to the size of 2 mm or larger, new blood vessels are formed around the tumor through which the supply of oxygen and nutrients and the removal of waste products are allowed (Fidler, I. J. et al., Cell, 79, 185 (1994)). In addition, the metastasis of cancerous cells can be accelerated through the vast capillary networks newly formed by various angiogenic factors secreted from cancerous cells or normal tissue cells (Biood, C. H. et al., Biochem. Biophys. Acta., 1032, 89 (1990)).

A limitation of conventional anticancer agents and chemical therapies is that various types of cancerous cells are present even in a single tumor and they have varying mutation and growth rates that are higher than those of normal cells and consequently they become resistant to the conventional anticancer agents. In contrast, anti-angiogenic therapies for cancer inhibit the growth of host normal cells (vascular endothelial cells), but not cancerous cells themselves, so that they are expected to overcome the problems of conventional therapies for cancer, which are due to the versatility and resistance of cancerous cells. Advantages of the antiangiogenic therapies to preexisting therapies for cancer is supported by various animal test results published by many researchers (Burrows, F. J. et al., Pharmac. Ther., 64, 155 (1994)).

In the body coexist angiogenic factors and antiangiogenic factors, through the balance of which angiogenesis is elaborately performed. Until now, there have been known dozens of cancer-relevant angiogenic factors, most of which do not act as growth factors for endothelial cells (Bussolino, F. et al., Trends. Biochem. Sci. 22, 251 (1997)). On the other hand, VEGF is known to act as an endothelial cell-specific growth factor in vitro (Gospodarowics, D, et al., Proc. Natl, Acad. Sci., USA, 86, 7311 (1989)), increases vascular permeability (Leung, D. W. et al., Science, 246, 1306 (1989), and induces the angiogenesis related to the progress of cancer in vivo (Plouet, J. et al., EMBO J., 8, 3801 (1989)).

It is revealed that VEGF is one of the most potent, angiogenic factors, whose expression is induced by a variety of stimuli, including hypoxia, and is indispensably required for the growth and metastasis of human cancerous cells in vivo (Connolly, D. T. et al., J. Biol. Chem. 264, 20017 (1989); Kim, K. J. et al., Nature 362, 841 (1993)). VEGF binds to heparin and shares homology in amino acid sequence with PLGF (placental growth factor) and PDGF (platelet-derived growth factor) (Conn, G. et al., Proc. Natl. Acad. Sci., USA, 87, 2628 (1990); Keck, P. I. et al., Science, 246, 1309 (1989); Maglione, D. et al., Proc. Natl. Acad. Sci., USA, 88, 9267 (1991)). Also, it is known that VEGF is expressed as four isoforms consisting of 121, 165, 189, and 206 amino acids, respectively, by alternative splicing (Tischer, E. et al., J. Biol. Chem., 266, 11947 (1991)), of which the $VEGF_{121}$ is not associated with heparin.

The signal transduction pathway of VEGF by which it exerts its functions as a growth factor starts with the binding of VEGF to cellular receptors (KDR/Flk-1 and Flt-1) which are specifically expressed on vascular endothelial cells (Millauer, B. et al., Cell, 72, 835 (1993), De Vries, C., et al., Science 255, 989 (1992)). The significance of VEGF in vasculogenesis during embryogenesis and in angiogenesis has been demonstrated by gene deletion studies of VEGF and VEGFR, (Fong, G. h. et al., Nature, 376, 66 (1995); Shalaby, F. et al., Nature, 376, 62 (1995); Carmeliet, P. et al., Nature, 380, 435 (1996); Ferrara, N. et al., Nature, 380, 439 (1996)), the malignant transformation of cancerous cells upon over-expression of VEGF in cancer cells (Zang, H. T. et al., J. Natl. Cancer Inst., 87, 213 (1995)), and the inhibition of the growth of cancer cells by neutralizing anti-VEGF monoclonal antibodies and by the expression of soluble Flt-1 and dominant-negative KDR/FlK-1 (Kim, K. J. et al., Nature, 362, 841 (1993); Goldman, C. K. et al., Proc. Natl. Acad. Sci., USA, 95, 8975 (1998)). In addition, there are reported other research results which prove that VEGF plays a key role in angiogenesis.

Therefore, materials which act to inhibit the association between VEGF and its receptors can suppress the angiogenesis driven by VEGF as well as the growth and metastasis of cancer cells, which secrete VEGF (Martiny-Baron, G. et al., Curr. Opin. Biotechnol., 6, 675 (1995)).

SUMMARY OF THE INVENTION

It is an object of the present invention to provide a VEGF-antagonistic peptide which is able to inhibit angiogenesis and the growth and metastasis of cancer cells.

BRIEF DESCRIPTION OF THE DRAWINGS

FIG. 10b is a histogram in which the radioactivity of the thymidine incorporated into the genome of HUVEC is measured in the absence of peptides and in the presence of 100 μM of each of the three peptides, demonstrating that the inhibition of cell growth is not attributed to the cytotoxicity of the peptides.

DETAILED DESCRIPTION OF THE INVENTION

Figure 1A:
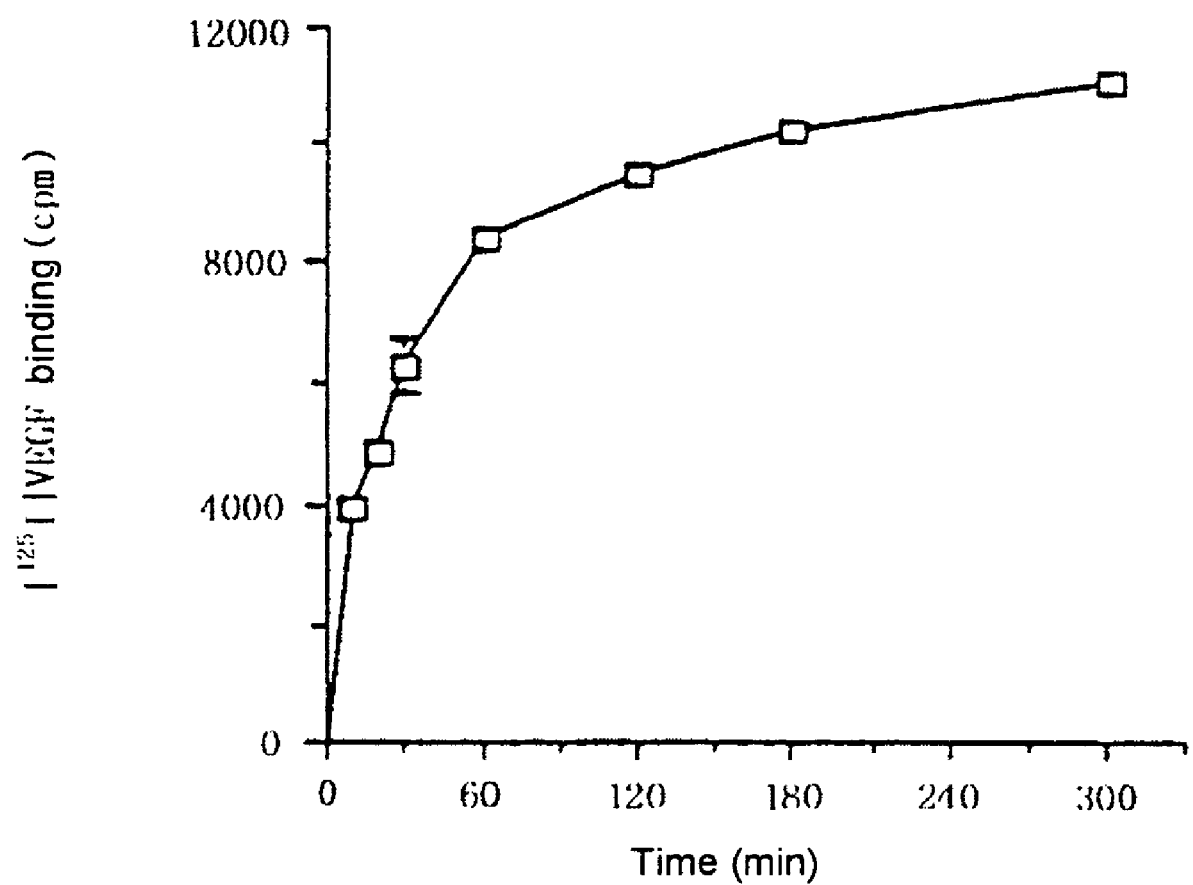
FIG. 1a is a curve showing that $^{125}$I-labeled VEGF binds to its receptors on the surface of HUVEC (human umbilical vein endothelial cells) in a time-dependent manner.

To separate new anti-VEGF peptides in the present invention combinatorial library of small peptides were used, from which the development of small molecule drug candidates has proven remarkably successful (Gho, Y. S. et al., Cancer Res., 57, 3733 (1997); Park, J. Y. et al., Endocrinology, 138, 617 (1997)).

To begin with, a peptide combinatorial library is constructed. In this regard, there are synthesized hexa-peptides in which 19 kinds of amino acids are specified at each amino acid position. If a specific amino acid residue at a determined position and other amino acid residues at the other positions in the hexa-peptides are represented by O and Xs, respectively, the peptides can be expressed as $OX_2X_3X_4X_5X_6, X_1OX_3X_4X_5X_6, \ldots X_1X_2X_3X_4X_5O$, which amounts to 114 (6×19) combinations.

From the combinatorial peptide library are separated the peptide sequences which inhibit at the highest efficiency the binding of VEGF to its receptors present on vascular endothelial cells. In the present invention, a radioactive iodine-labeled VEGF, along with the combinatorial peptide library, is added to a culture of vascular endothelial cells and allowed to react with one another. After the removal of unbound VEGF, quantification of the bound VEGF to the receptors present on the endothelial cell surface is performed by measuring the radioactivity of the associated VEGF. The peptide sequences are selected which show inhibitory activity against the binding of VEGF to its receptors, at the lowest concentrations.

The soluble hexa-peptide library were tested through the selection procedure described above (FIG. 2). The amino acids at each position of the hexa-peptides that show significant contribution to the inhibition are listed in Table 1, below.

TABLE 1

| 1(N) | 2 | 3 | 4 | 5 | 6 |
|---|---|---|---|---|---|
| K | K | K | R | K | R |
| R | R | R | K | R | K |
| G | H | H | H | W | H |
| A | T | T |   |   | F |
| H | W | W |   |   | L |

Based on the results from the above primary selection, as seen in the following Table 2, peptide sequences are synthesized in such a way that the two amino acids from carboxy termini are specified by selected amino acids while the other positions are occupied by the random mixture of the amino acid residues selected through the primary selection procedure in equal ratios.

TABLE 2

|   | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| 1-N |   |   |   |   |   | Mixture of K, R, G, A, H |   |   |   |    |    |    |    |    |    |
| 2 |   |   |   |   |   | Mixture of K, R, H, T, W |   |   |   |    |    |    |    |    |    |
| 3 |   |   |   |   |   | Mixture of K, R, W, G, S |   |   |   |    |    |    |    |    |    |
| 4 |   |   |   |   |   | Mixture of R, K, H |   |   |   |    |    |    |    |    |    |
| 5 | K | R | R | K | K | K | H | H | H | F  | F  | F  | L  | L  | L  |
| 6-C | R | R | W | K | R | W | K | R | R | K  | R  | W  | K  | R  | W  |

Figure 3A:
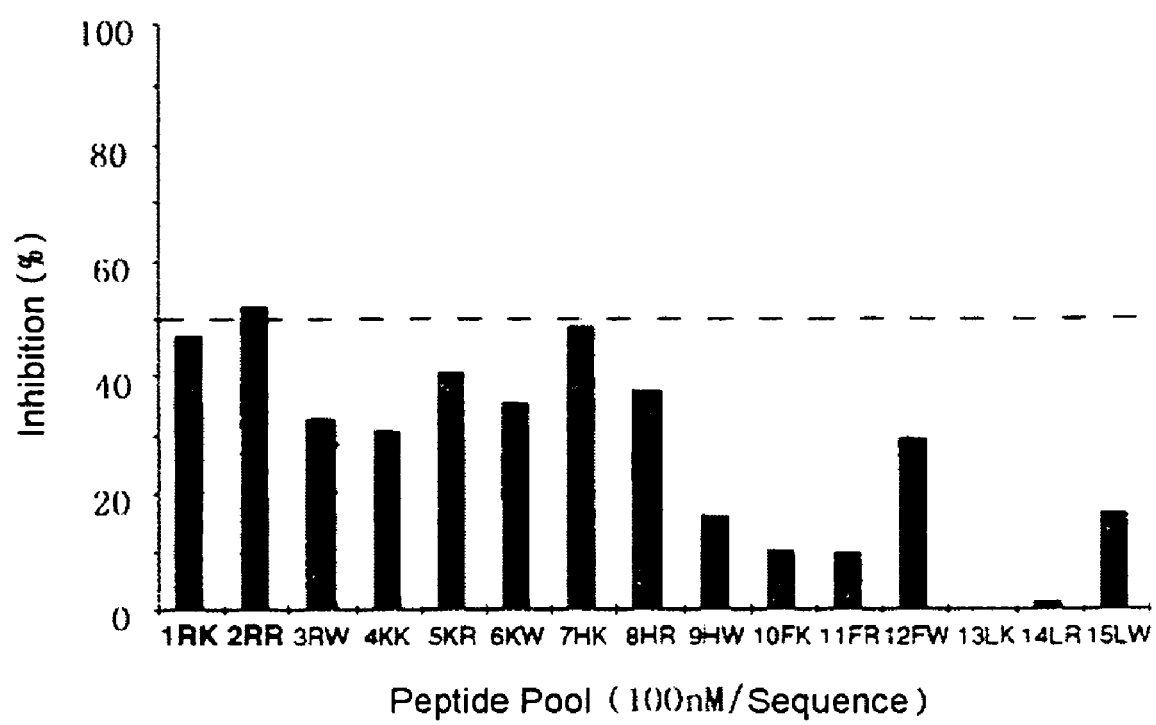
FIG. 3a is a histogram in which the inhibitory activity of the first secondary pool of peptides, synthesized on the basis of the primary searching results, against the binding of VEGF to its receptors is represented according to amino acid residues when the pool is used at a concentration of 100 nM/peptide.

Again, the first sub-library is tested for the inhibitory activity against the binding of VEGF to its receptors (see FIG. 3a). According to this quantitative data, the peptide sequences which were found to inhibit the binding with the highest efficiency were those with arginine or histidine at their sixth position and arginine or lysine at their fifth position.

On the basis of the above two selection procedures, the second sub-library is constructed in such a way that the first, the fourth and the sixth positions are specified by predetermined amino acids while the other three positions are occupied by the amino acid mixtures secured through the above two selection procedures, as shown in Table 3, below.

An examination which was made for the inhibitory activity of the 12 peptides against the binding of VEGF to its receptors verified that the peptide of sequence 1 (SEQ ID NO: 1) ($NH_2$-Arg-Arg-Lys-Arg-Arg-Arg-$CONH_2$), the peptide of sequence 2 (SEQ ID NO: 2) ($NH_2$-Arg-Lys-Lys-Arg-Lys-Arg-$CONH_2$), and the peptide of sequence 3 (SEQ ID NO: 3) ($NH_2$-Arg-Arg-Arg-Arg-Arg-Arg-$CONH_2$) are the most potent inhibitors against VEGF activity.

There may be various mechanisms through which the peptides can inhibit VEGF from binding to its receptors. In order to elucidate the accurate inhibitory mechanism, an examination was made of the possibility that the identified peptides could directly associate with VEGF to inhibit the

TABLE 3

|   | 1 | 2 | 3 | 4 | 5 | 6 | 7 | 8 | 9 | 10 | 11 | 12 | 13 | 14 | 15 |
|---|---|---|---|---|---|---|---|---|---|----|----|----|----|----|----|
| 1-N | K | R | G | A | H | K | R | G | A | H  | K  | R  | A  | G  | H  |
| 2 |   |   |   |   |   | Mixture of K, R, H, T, W |   |   |   |    |    |    |    |    |    |
| 3 |   |   |   |   |   | Mixture of K, R, W, G, S |   |   |   |    |    |    |    |    |    |
| 4 | R | R | R | R | R | K | K | K | K | K  | H  | H  | H  | H  | H  |
| 5 |   |   |   |   |   | Combinatorial library K, R |   |   |   |    |    |    |    |    |    |
| 6-C | R | R | R | R | R | R | R | R | R | R  | R  | R  | R  | R  | R  |

Figure 3B:
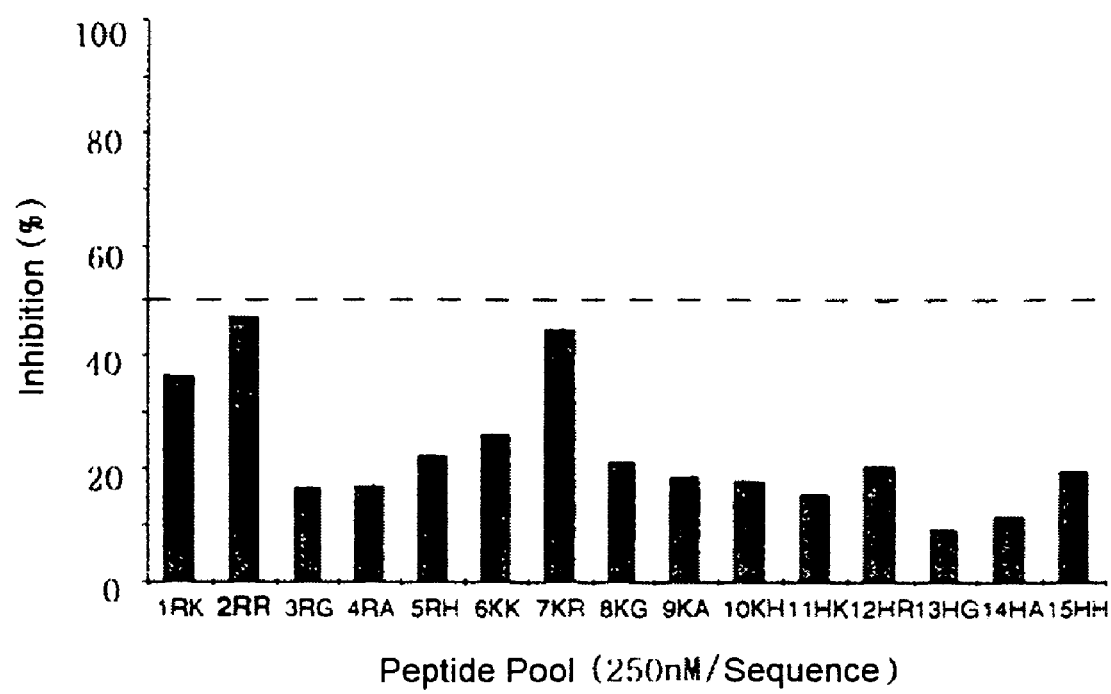
FIG. 3b is a histogram in which the inhibitory activity of the second secondary pool of peptides, synthesized on the basis of the results of FIG. 3a, against the binding of VEGF to its receptors is represented according to amino acid residues when the pool of peptides is used at a concentration of 250 nM/peptide.

Analysis for the inhibitory activity against the activity of VEGF reveals that the peptides in which the first, the fourth and the sixth positions are all specified by arginine inhibit the binding of VEGF to its receptors with the most efficiency (see FIG. 3b).

Figure 4:
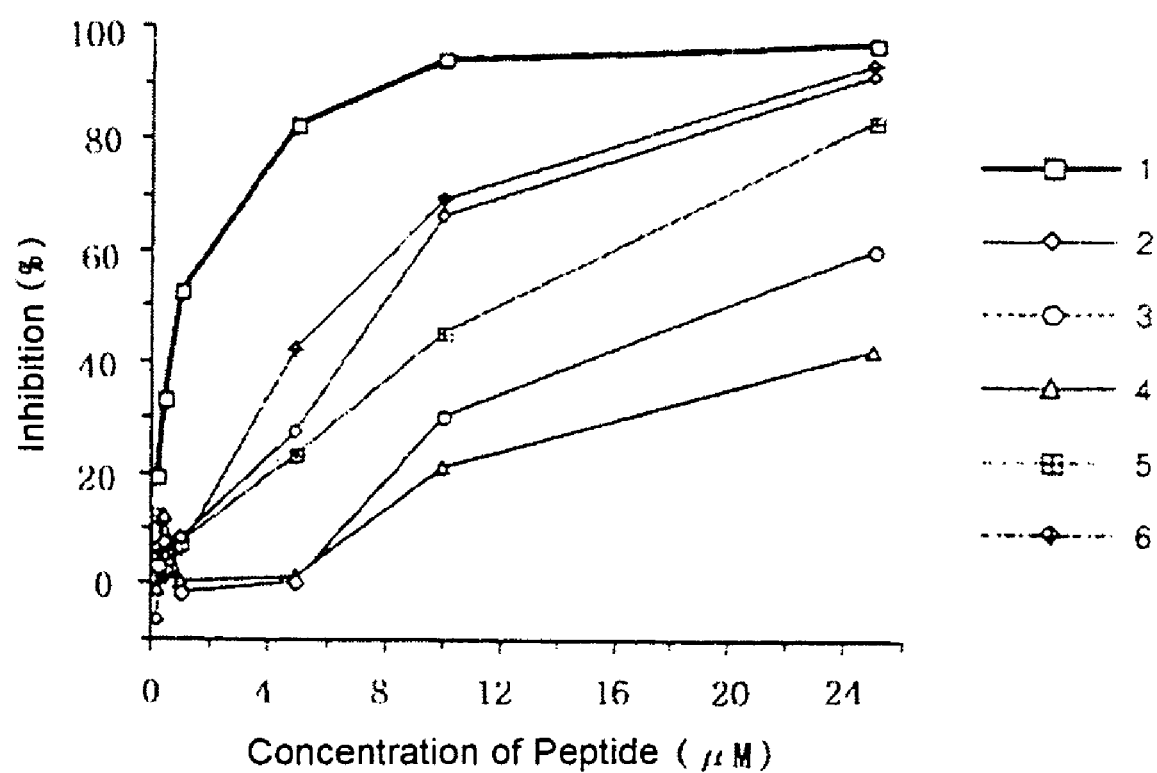
FIG. 4 shows curves in which the inhibition activity of six fractions separated from a mixture of the most effective peptides selected from the second secondary pool through a $C_{18}$ reverse-phase column according to the retention time. The Inhibitory activity of each fraction against the binding of VEGF to its receptors, is plotted versus concentration of the fractions.

Thereafter, additional analysis of the peptide mixtures, obtained after separation by use of a $C_{18}$ reverse-phase column, for inhibitory activity against the binding of VEGF to its receptors led to the conclusion that the most effective inhibitory activity is induced when the first, the fourth and the sixth positions all are occupied by arginine, the second position by arginine, lysine or histidine, and the third and the fifth positions by arginine or lysine (see FIG. 4).

These preferable combinations for the amino acid sequence are shown in Table 4, below.

binding of VEGF to its receptors present on cell surfaces of vascular endothelial cells. In this connection, labeled VEGF and non-labeled VEGF were allowed to competitively associate with immobilized peptides. From the quantification of radioactivity from the immobilized peptides, the association extent between labeled VEGF and the peptides was found to decrease with increase of the concentrations of non-labeled VEGF and free peptides added, demonstrating that the identified peptides of the present invention directly associate with VEGF. The finding that the association between a peptide and labeled VEGF is completely inhibited by all of the three peptides makes it possible to postulate that the peptides of sequence 1, sequence 2, and sequence 3 have identical or overlapped binding domains on VEGF (FIGS. 7

TABLE 4

|   | 1 | 2 | 3 | 4 | 5 | 6 | 7 | 8 | 9 | 10 | 11 | 12 |
|---|---|---|---|---|---|---|---|---|---|----|----|----|
| 1(R)-N | R | R | R | R | R | R | R | R | R | R  | R  | R  |
| 2(K, R, H) | K | R | H | K | R | H | K | R | H | K  | R  | H  |
| 3(K, R) | K | K | K | R | R | R | K | K | K | R  | R  | R  |
| 4(R) | R | R | R | R | R | R | R | R | R | R  | R  | R  |
| 5(K, R) | K | K | K | K | K | K | R | R | R | R  | R  | R  |
| 6(R)-C | R | R | R | R | R | R | R | R | R | R  | R  | R  |
| $IC_{50}(\mu M)$ | 3.4 | 6.0 | >20 | 8.5 | 4.5 | >20 | 6.5 | 2.0 | >20 | 7.8 | 3.8 | >20 | and 8). Also, a quantitative measurement was made of the inhibitory activity of the peptide of sequence 3 against the association between 5 types of VEGF isoforms and their receptors, leading to the conclusion that both the amino and the carboxyl terminals of $VEGF_{121}$ are important to the binding domain (see FIG. 9).

In order to determine whether the peptides of the present invention inhibit the VEGF-stimulated growth of vascular endothelial cells, the amount of DNA synthesized in vascular endothelial cells in the presence of the screened peptides and VEGF was measured. As a result, it was obtained that the peptides of the present invention inhibit the DNA synthesis induced by VEGF in vascular endothelial cells in a dose-dependent pattern. In consequence, the peptides of the present invention have inhibitory activity against the VEGF-stimulated growth of vascular endothelial cells (see FIGS. 10a and 10b).

In an experiment, egg CAM (chorioallantoic membrane) was treated with VEGF in the presence of the peptide of the present invention to give data which show that VEGF-induced angiogenesis is inhibited by the peptides, thus verifying the anti-angiogenic activity of the peptides of the present invention. Additionally, in an animal test for angiogenesis using rabbit cornea, the angiogenesis which was definitely observed from the control group treated with only VEGF was completely inhibited in the group treated with VEGF and the peptides simultaneously (see FIG. 11). Further, an experiment was conducted to determine whether the peptides of the present invention are able to inhibit the angiogenesis induced by VEGF secreted from cancer cells. To this end, VEGF-secreting sarcoma was applied, along with the peptides of the present invention, to egg CAM. The inhibitory effect of the peptides of the present invention on the cancer cell-induced angiogenesis was observed (see FIG. 12).

Figure 13:
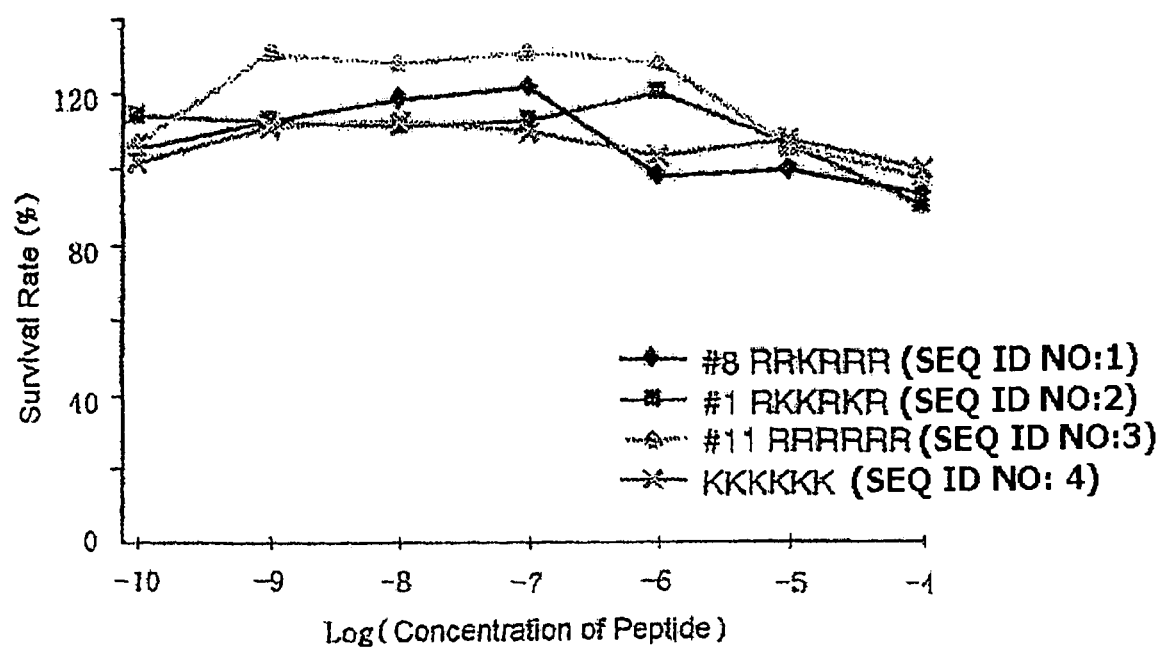
FIG. 13 shows curves in which viability of human fibro sarcoma cell line is plotted versus concentrations of peptides, demonstrating that the peptides of the invention (SEQ ID NO: 1, SEQ ID NO: 2, and SEQ ID NO: 3, wherein control peptide KKKKKK has SEQ ID NO: 4), have no direct influence on human fibro sarcoma cells.

An experiment was conducted to see whether the peptides of the invention, which were proved to have antagonistic activity to VEGF, have direct inhibitory effects on the growth of cancer cells. In the experiment, human fibro sarcoma cells were cultured and treated with the peptides of the present invention, followed by measuring cell viability. From the measurements, it is apparent that the peptides of the present invention have no direct influence on the growth of the fibro sarcoma cells, as seen in FIG. 13.

The peptides of the present invention were also investigated as to the ability to inhibit the growth and metastasis of cancer cells. Along with the peptides of the present invention, human colon cancer cells were introduced to mice by subcutaneous injection. After a certain period of time, the tumors formed were measured for size. It was observed that a significant reduction was brought about in the size of the tumor formed in the mice treated with the peptides of the present invention, compared to the control group treated with phosphate buffered saline only (see FIG. 14). In addition, when cancer cells implanted into the spleen of mice were treated with the peptides of the present invention, better results were obtained in the number of metastatic tumor nodules in liver and the weight of the liver than when the implanted cells were treated only with phosphate buffered saline (see FIGS. 15a and 15b). From the above experimental results, the peptides of the present invention can be assumed to exert their inhibitory activity against the growth and metastasis of malignant tumors by shielding the signal transduction pathway of VEGF.

In conclusion, through the above various experiments, it was revealed that the peptides of the present invention do not directly affect the growth of cancer cells, but specifically suppress the angiogenesis induced by cancer cells as a result of the inhibitory activity of the peptides against the binding of VEGF secreted from cancer cells to receptors present on vascular endothelial cell surface.

Thanks to superior ability to inhibit the binding of VEGF to its receptors, the peptides of the present invention can be used as therapeutics for angiogenesis-related diseases, including cancer, diabetic retinopathy, rheumatoid arthritis, etc.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Characterization of $^{125}$I-Labeled VEGF

Utilizing $^{125}$I-labeled $VEGF_{165}$ in various experiments, an examination was made as to whether this labeled protein have the same activity as that of natural VEGF protein.

First, HUVEC (human umbilical vein endothelial cells) (Clonetics) were placed on gelatin-coated 100 mm dishes (Falcon) containing a vascular endothelial cell culture medium (Medium 199+20% BCS, 5 µg/ml of heparin, 6 µg/ml of endothelial cell growth supplement, 5 ng/ml of basic fibroblast growth factor) and cultured at 37° C. in a $CO_2$ incubator for animal cell culture. After a certain period of time, the cells were treated with trypsin/EDTA. After centrifugation, the cells harvested were suspended in a fresh, vascular endothelial cells culture medium and aliquoted at a density of $5\times10^4$ cell/well to a 24 well plate (Costar Co.). Following one-day culturing, the cells were added in a binding medium (Medium 199/25 mM HEPES, pH 7.4/ 0.1% bovine serum albumin) containing 0.2 ng of $^{125}$I-labeled $VEGF_{165}$ and reacted at 4° C. for 3 hours. To remove the labeled VEGF which still remained in the medium, the cells were washed twice with the same medium as used above, and once with PBS containing 0.1% albumin. Thereafter, to quantitatively determine the amount of the labeled VEGF which bound to receptors present on the surface of the vascular endothelial cells, the cells were treated with 0.5 ml of a lysis solution (20 mM Tris-HCl, pH 7.4/1% TritonX-100) for 20 min, followed by measuring the resulting lysate for radioactivity with the aid of a γ-counter. As for the non-specific binding, it was determined from a cell group cultured in the presence of a mixture of the labeled VEGF and non-labeled VEGF in a molar ratio of 1:100. This cell group was cultured as a negative control.

Figure 1B:
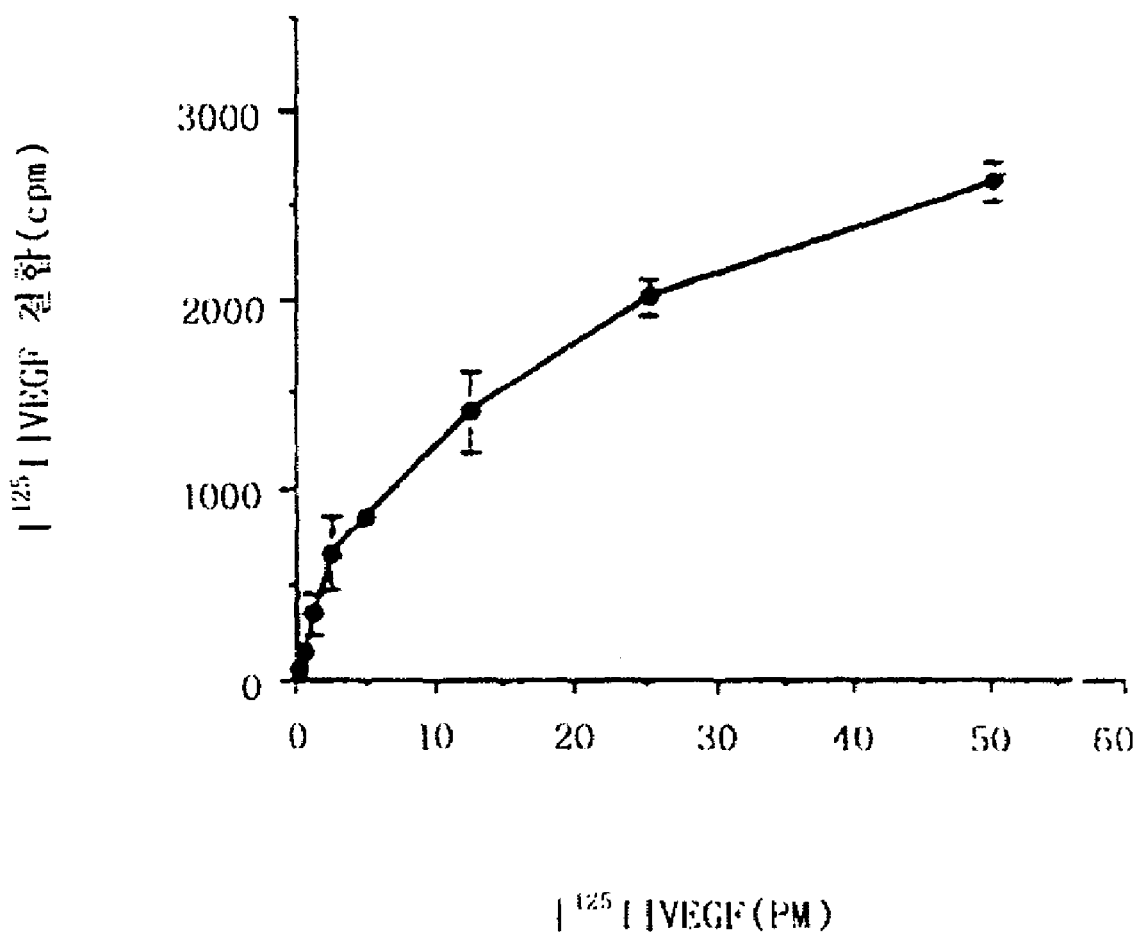
FIG. 1b is a curve showing that $^{125}$I-labeled VEGF binds to its receptors on the surface of HUVEC in a dose-dependent manner.

The measurement results are shown in FIGS. 1a and 1b in which radioactivity is plotted versus time and concentration, respectively. As seen in these figures, the binding of labeled VEGF (1 ng/ml) to VEGF receptors present on the surface of HUVEC ($5\times10^4$ cells/well) behaves in a time-dependent pattern and a VEGF dose-dependent pattern, demonstrating that the interaction between VEGF and its receptors are specific.

Figure 1C:
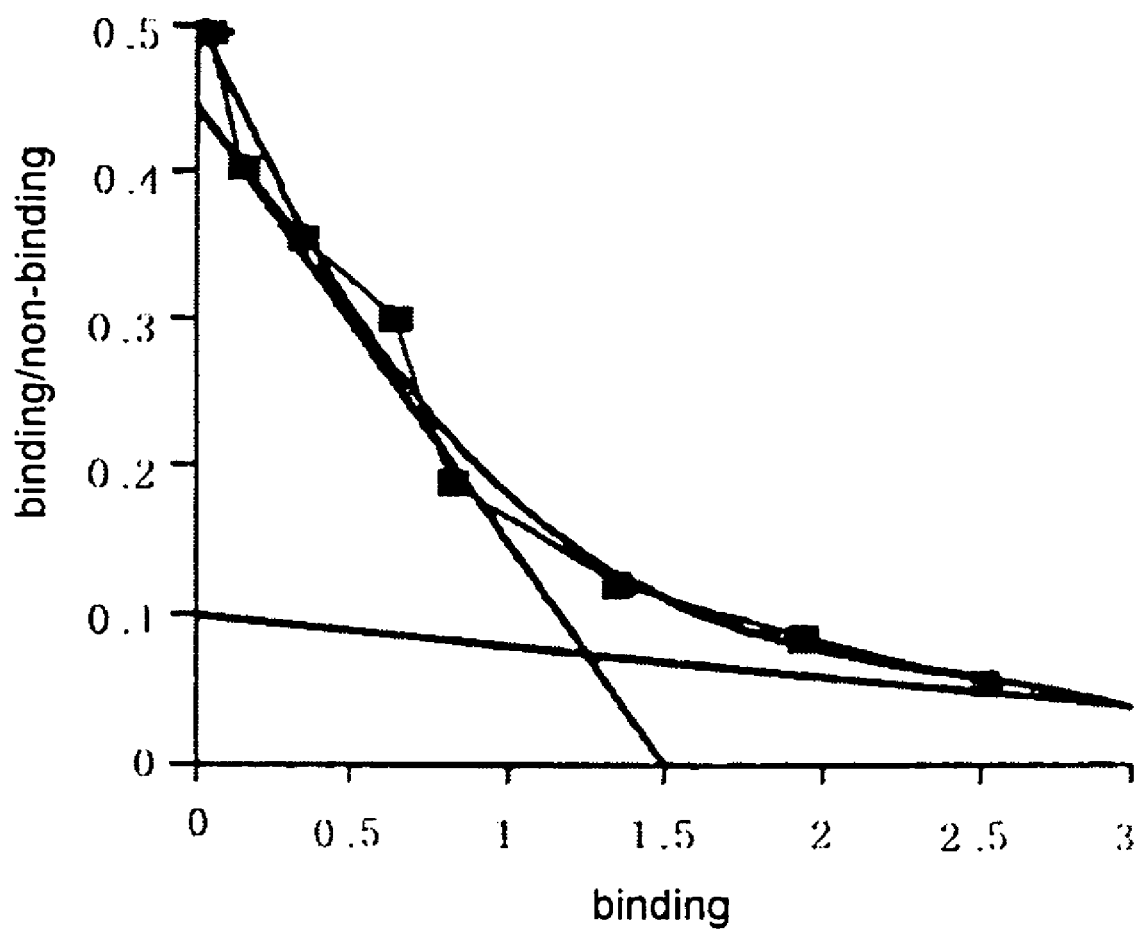
FIG. 1c is a Scatchard plot obtained from the results of FIG. 1b, which shows that two kinds of VEGF receptors exist on the surface of vascular endothelial cells.

Scatchard analysis of the results obtained in FIG. 1b revealed that two kinds of receptors exist on the surface of vascular endothelial cells, as seen in FIG. 1c. One of two kinds of the receptors has a dissociation constant (KD) of 3 pM and is populated at a density of about 2,000 per cells while the other has a dissociation constant (KD) of 50 pM and is populated at a density of about 6,000 per cell. These results agree with those reported from various studies (Maciag, T. et al., Proc. Natl. Acad. Sci., USA, 76, 5674 (1979); Myoken, Y. et al., Proc. Natl. Acad. Sci., USA, 88, 5819 (1991); Gengrinovitch, S. et al., J. Biol. Chem., 270, 15059 (1996); Bikfalvi, A. et al., J. Cell Physiol. 149, 50 (1991)).

Example 2

Search from Combinatorial Peptide Library for VEGF-Antagonistic Peptide Sequence Step 1: Construction of Peptide Combinatorial Library A peptide combinatorial library was constructed according to a known method (Pinilla, C. et al., Bio techniques, 13, 901 (1992)).

When a library consisting of hexa-peptides were synthesized, a predetermined amino acid residue was assigned to a specific one of the six positions while the other five positions were occupied by any of 19 kinds of amino acids (exclusive of cystein). Supposing that a specific amino acid residue at a determined position and other amino acid residues at the other positions in the peptides of six amino acid residues were represented by O and Xs, respectively, the peptides were expressed as $OX_2X_3X_4X_5X_6$, $X_1OX_3X_4X_5X_6$, . . . $X_1X_2X_3X_4X_5O$. That is to say, in peptides of six amino acid residues, 19 kinds of amino acids are specified at each amino acid position while non-specified positions were occupied by any of amino acids exclusive of cystein to construct libraries of peptides, which amount to 114 (6×19) combinations.

Step 2: Primary Search for Peptide Sequences

To select the peptides which can combine with VEGF from the combinatorial peptide libraries, the following experiment was conducted.

On a 24-well plate (Costar Co), HUVEC (human umbilical vein endothelial cells) (Clonetics) were cultured in a medium at a density of $5 \times 10^4$ cells/well for one day. Then, the cells were transferred to a medium (Medium 199/25 mM HEPES, pH 7.4/0.1% bovine serum albumin) containing 0.2 ng of $^{125}$I-labeled VEGF and various concentrations of peptides or combinatorial peptide libraries and reacted at 4° C. for 3 hours. The cells were washed twice with the same medium and once with PBS containing 0.1% albumin to remove the labeled VEGF which still remained uncombined. Thereafter, to quantify the labeled VEGF which bound to receptors present on the surface of the vascular endothelial cells, the cells were treated with 0.5 ml of a lysis solution (20 mM Tris-HCl, pH 7.4/1% TritonX-100) for 20 min, followed by measuring the resulting lysate for radioactivity with the aid of a γ-counter.

Figure 2:
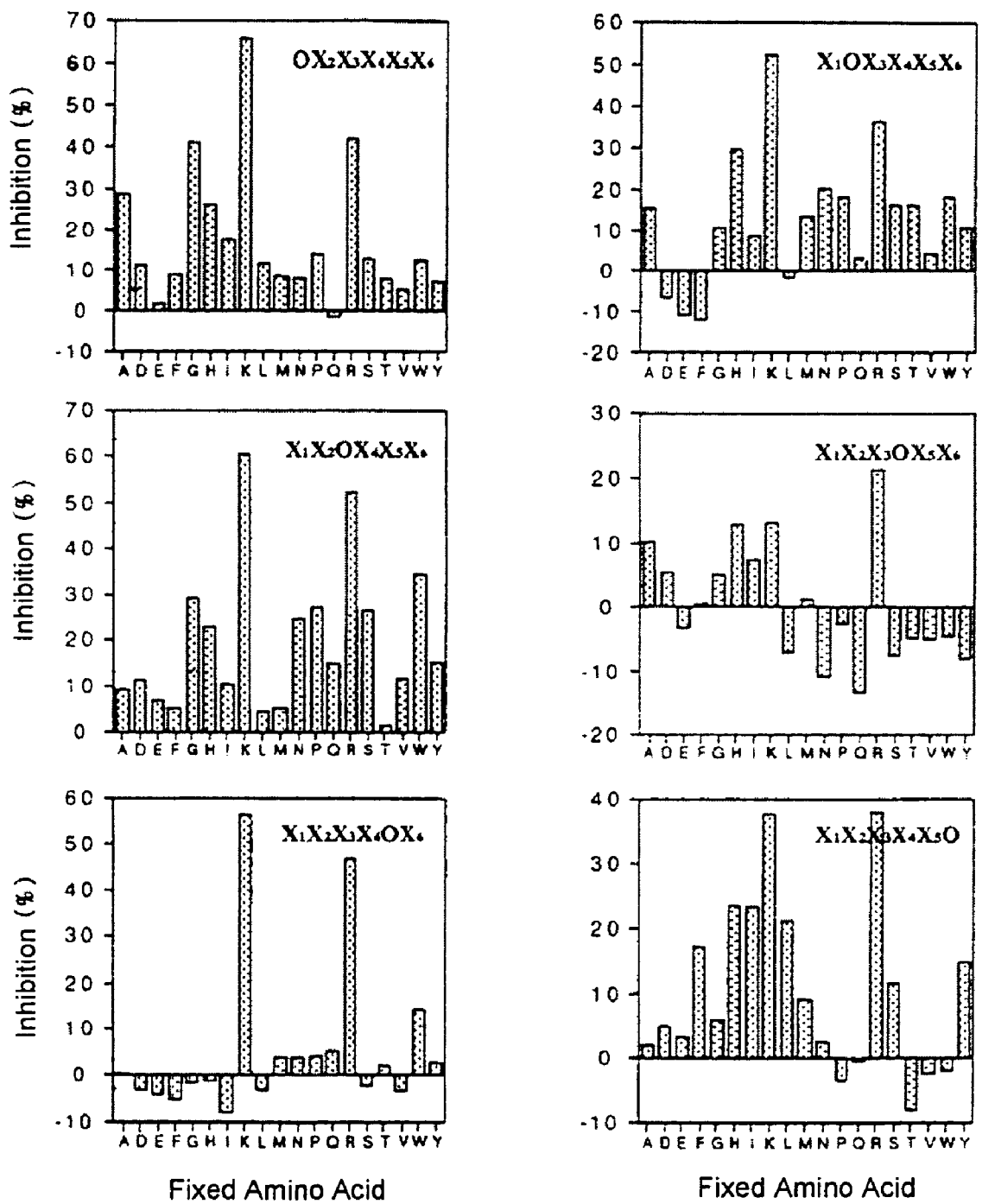
FIG. 2 provides histograms showing a primary searching results, in which the inhibitory activity of combinatorial peptide libraries against the binding of VEGF to its receptors is represented according to amino acid residues on each position of the hexa-peptide when combinatorial peptide libraries are used at a concentration of 0.33 nM/peptide.

With reference to FIG. 2, percent inhibition of combinatorial peptide libraries against the binding of VEGF to its receptors is represented according to amino acid residues on each position of the hexa-peptide when combinatorial peptide libraries are used at a concentration of 0.33 nM/peptide. Based on these results, 3-5 amino acids were selected for each position. As seen, the most potent activity antagonistic to VEGF was observed when lysine or arginine occupied all positions of the peptide.

Step 3: Secondary Search for Peptide Sequences

Based on the primary search results, two pools of peptides were synthesized as seen in Tables 2 and 3. Again, these two combinatorial peptide libraries were examined for the antagonistic activity against the binding of VEGF to its receptors and the results are given in FIGS. 3a and 3b.

First, in order to make the first secondary pools of peptides, the two carboxyl terminal positions were specified by selected amino acids while the other positions were allowed to be occupied by the amino acid residues selected through the secondary selection in equal ratios. Amounting to 375 sequences in total, this first secondary pool of peptides was composed of 15 combinatorial peptide libraries according to the combination of the two carboxyl terminal amino acids.

As in the primary search, this first secondary pool of peptides was examined at various concentrations (0.01, 0.05, 0.1, and 1 μM/sequence) for the antagonistic activity against VEGF binding. With reference to FIG. 3a, percent inhibition of peptide combinatorial libraries against the binding of VEGF to its receptors is represented according to amino acid residues on the fifth and the sixth positions of the hexa-peptide when the first secondary pool of peptides were used at a concentration of 0.1 μM/peptide. As seen in FIG. 3a, the peptide sequences which inhibited the binding with the highest efficiency were those with arginine or histidine at their sixth position and arginine or lysine at their fifth position.

Next, the second secondary pools of peptides was constructed by taking advantage of the results obtained through the two selection procedures. The first, the fourth, and the sixth positions from the amino end were specified by predetermined amino acids while the amino acid residue data was utilized for the other three positions, as shown in Table 3.

Combination of the specified amino acid residues resulted in 15 combinatorial libraries, each consisting of 50 sequences. The antagonistic activity of the peptides was examined at various concentrations (0.1, 0.25, and 1 μM/sequence). With reference to FIG. 3b, percent inhibition of combinatorial peptide libraries against the binding of VEGF to its receptors is represented according to amino acid residues on the first, the fourth, and the sixth positions of the hexa-peptide when the second secondary pool of peptides were used at a concentration of 0.25 μM/peptide. As seen in FIG. 3b, the most potent antagonistic activity to the binding of VEGF to its receptors was found in the sequences in which arginine occupied the first, the fourth, and the sixth positions all.

Step 4: Separation of Peptide Sequences

A mixture of the most effective peptides selected from the second secondary pool was separated through a $C_{18}$ reverse-phase column into six fractions by the retention time in the column. Again, each of the six fractions was examined for the influence on the binding of VEGF to its receptors at various concentrations (0.5, 1, 2, 5, 10, and 25 μM/peptide). The results are given in FIG. 4, which shows curves plotted by the percent inhibition versus concentration of the peptide fractions.

In the curves, the fraction 1 has the highest antagonistic activity. Also, the fraction 1 was identified to contain no tryptophan as no absorbance at $UV_{280}$, was detected. Qualitative analysis of its amino acid sequences proved the presence of arginine, lysine, and histidine.

Therefore, the data obtained thus far demonstrated that the six-amino acid sequences with arginine at all of the first, the fourth and the sixth positions are the most antagonistic to the binding of VEGF to its receptors while the most effective candidates for the other positions can be narrowed to two or three amino acid residues, e.g., arginine, lysine, and histidine for the second position, lysine and arginine for the third position, and arginine and lysine for the fifth position.

Resulting from the combination of the candidates, 12 peptides which were specified at the three positions by arginine were synthesized as shown in Table 4, followed by separating each peptide through a $C_{18}$ reverse-phase column.

Step 5: Tertiary Search for Peptide Sequences

Figure 5:
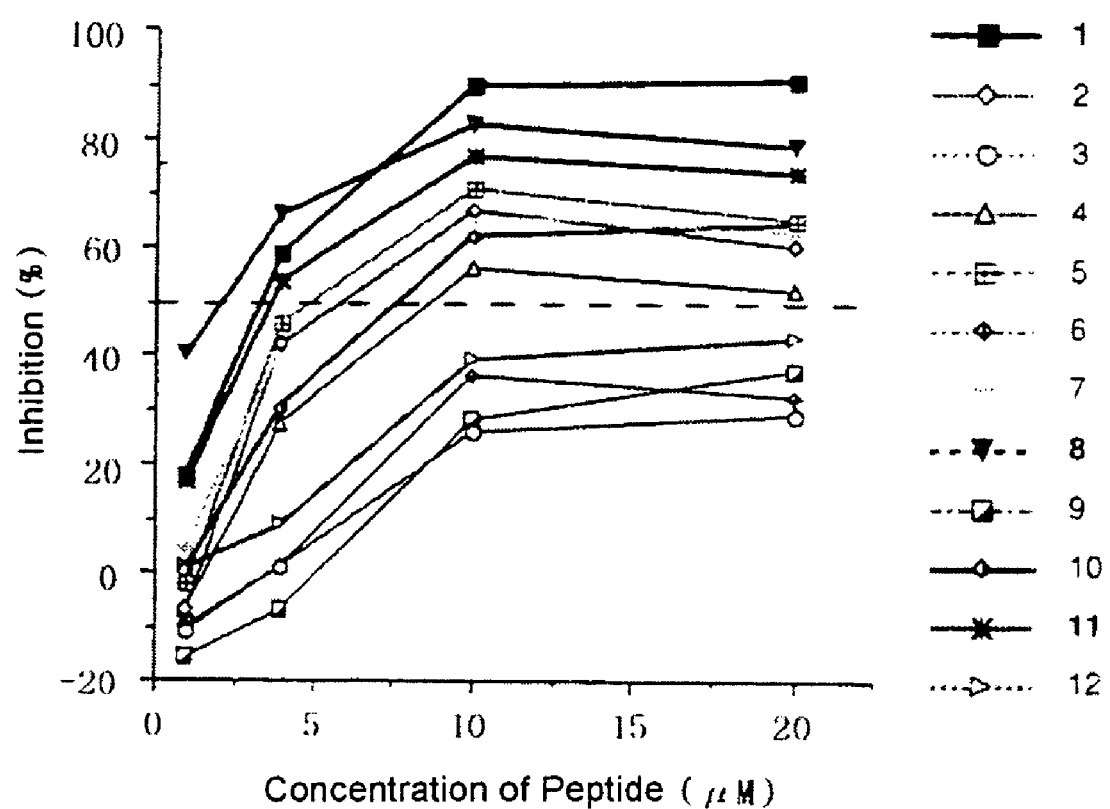
FIG. 5 shows curves in which the inhibitory activity of 12 peptides against the binding of VEGF to its receptors is plotted versus peptide concentration.

The sequence of each peptide was indirectly decided through the analysis of amino acid compositions and its concentration was determined, after which 12 peptides were assayed for antagonism toward VEGF binding at various concentrations (1, 4, 10, and 20 µM/sequence). The results are given in FIG. 5. As seen in FIG. 5, three peptides, Sequences 1, 2, and 3, were found to inhibit the binding of VEGF to its receptors at highest efficiency with $IC_{50}$ values of 2, 3.4, and 3.8 µM/sequence, respectively.

Figure 6:
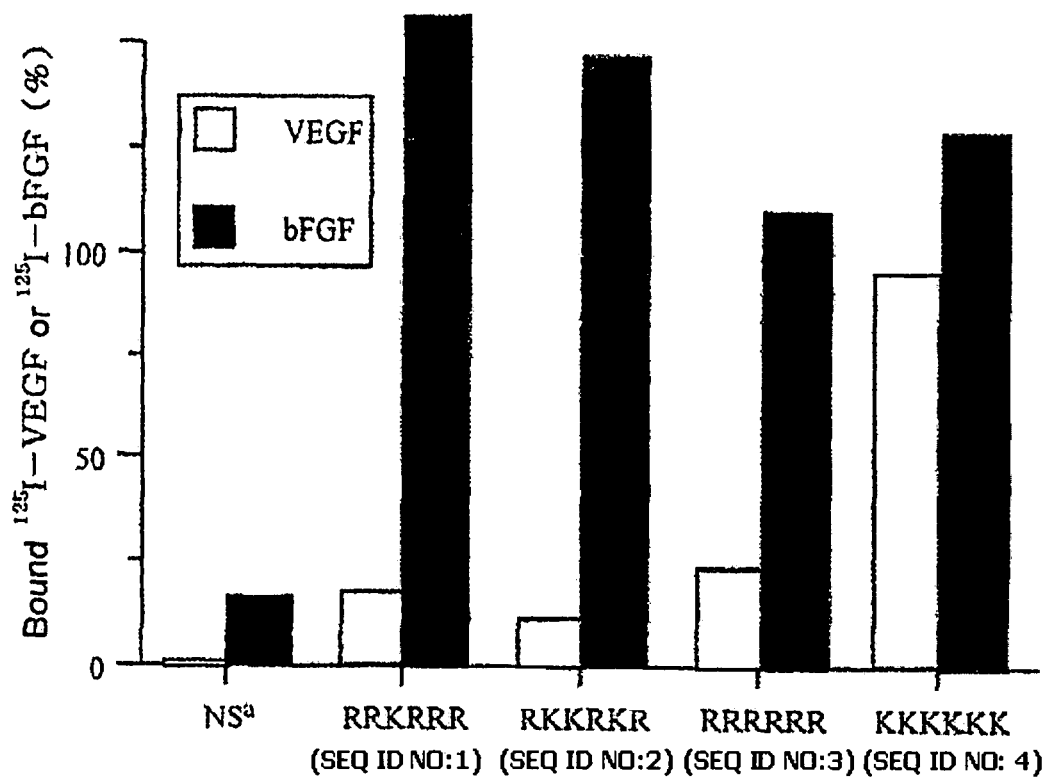
FIG. 6 is a histogram showing quantitative results for the binding of $I^{125}$-labeled VEGF and $I^{125}$-labeled bFGF (basic fibroblast growth factor) to their receptors in the presence of selected three peptides (SEQ ID NO: 1, SEQ ID NO:2, and SEQ ID NO: 3) or other control peptides wherein control peptide KKKKKK has SEQ ID NO: 4.

With reference to FIG. 6, there are shown quantitative results for the binding of $I^{125}$-labeled VEGF and $I^{125}$-labeled bFGF (basic fibroblast growth factor) to their receptors in the presence of various peptides. Despite a high concentration (10 µM) of a control peptide consisting of only lysine, no inhibition was observed between the labeled VEGF and the its receptors, showing that the inhibitory activity of the three peptides determined above does not result from positively charged amino acids, but is attributed to specific amino acid sequences. When it is taken into account that none of the three peptides inhibit the binding of bFGF, an angiogenic factor similar to VEGF, to its receptors, it is proven that they are specific for VEGF only.

Example 3

Characterization of Peptides Screened from Combinatorial Peptide Libraries

There are various possible mechanisms to inhibit the binding of VEGF to its receptors. For instance, an inhibitor may be combined with either VEGF or one or more of its receptors, thereby inhibiting the interaction between VEGF and the receptor.

To verify the postulated mechanism in which the screened peptides might be associated directly with VEGF so as to inhibit VEGF from binding to its receptors present on the surface of vascular endothelial cells, the following experiments were conducted. Each of the hexa-peptides was fixed on a 96-well ELISA plate at a concentration of 100 ng/well in such a manner that a 20% acetic acid solution containing each peptide was dried in air. The plate was treated three times with a phosphate buffered saline containing 0.1% albumin for 3 min each time. A solution of $^{125}$I-labeled VEGF in the same phosphate buffered saline was added to the plate at a concentration of 0.2 ng/well and incubated at 37° C. for 1 hour to associate the labeled VEGF with the peptides. To remove the peptides remaining unassociated, the plate washed four times with the same phosphate buffered saline for 3 min per each time, followed by measuring radioactivity with the aid of a γ-counter. As for the non-specific binding, it was determined by incubation in the presence of either a mixture of the labeled VEGF and non-labeled VEGF or a mixture of the fixed peptide and unfixed peptide in a molar ratio of 1:100. This was set as a negative control.

Figure 7:
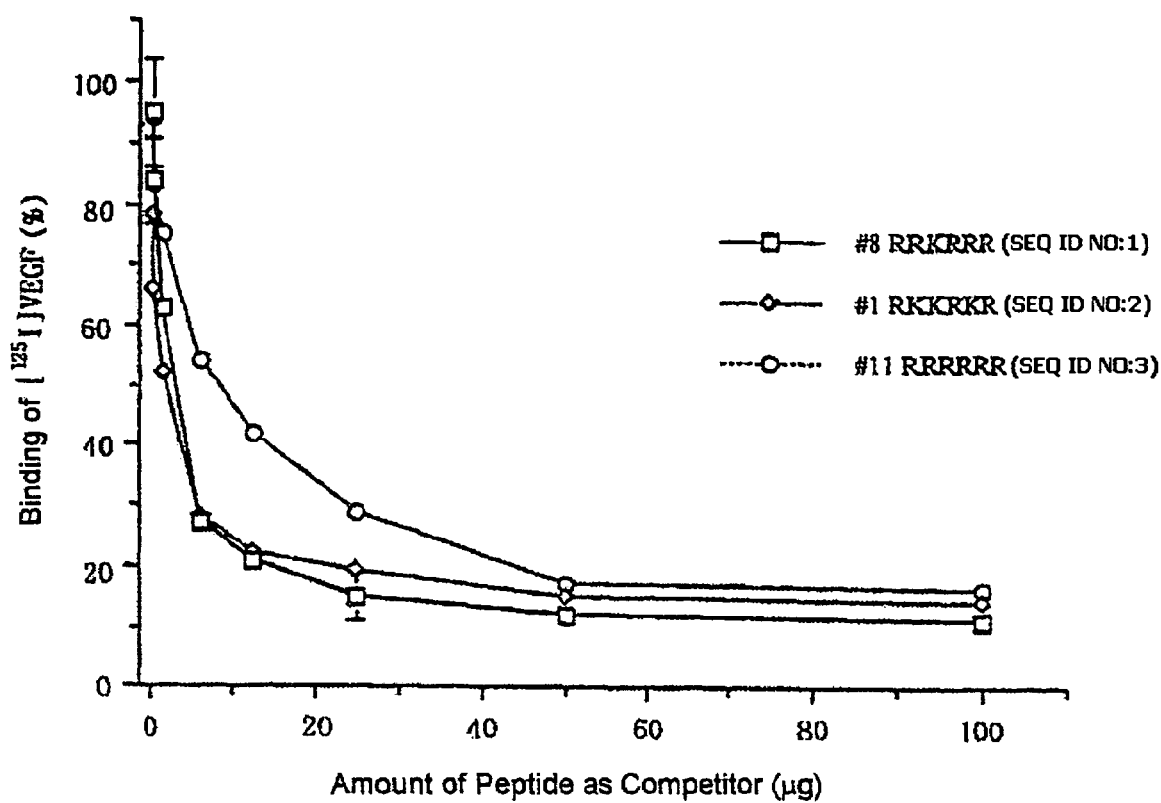
FIG. 7 shows curves in which radioactivity measured from $^{125}$I-labeled VEGF associated with fixed peptides (Sequences 1 (SEQ ID NO: 1), 2 (SEQ ID NO: 2), and 3 (SEQ ID NO: 3)) is plotted versus molar ratios of competitors (excess free peptides) to their counterparts.

With reference to FIG. 7, radioactivity measured from $^{125}$I-labeled VEGF associated with fixed peptides is plotted versus molar ratios of a competitor, such as non-labeled VEGF or free peptides, to its counterpart. As seen in the curves of FIG. 7, the radioactivity is in inverse proportion to the molar ratio, which demonstrates that the peptides directly associate with VEGF. The dissociation constant (KD) between VEGF and each peptide was determined using the $IC_{50}$ value according to the following formula (De Blasi, A. et al., Trends Pharmacol. Sci., 10, 227 (1989)).

$$KD=IC_{50}-[\text{non-labeled Competitor}]$$

The dissociation constants determined using the formula were 5 µM for Sequence 1, 2 µM for Sequence 2, and 22 µM for Sequence 3. From these results, it is apparent that all of the three peptides screened from the peptide combinatorial libraries associate with VEGF directly and specifically.

Figure 8:
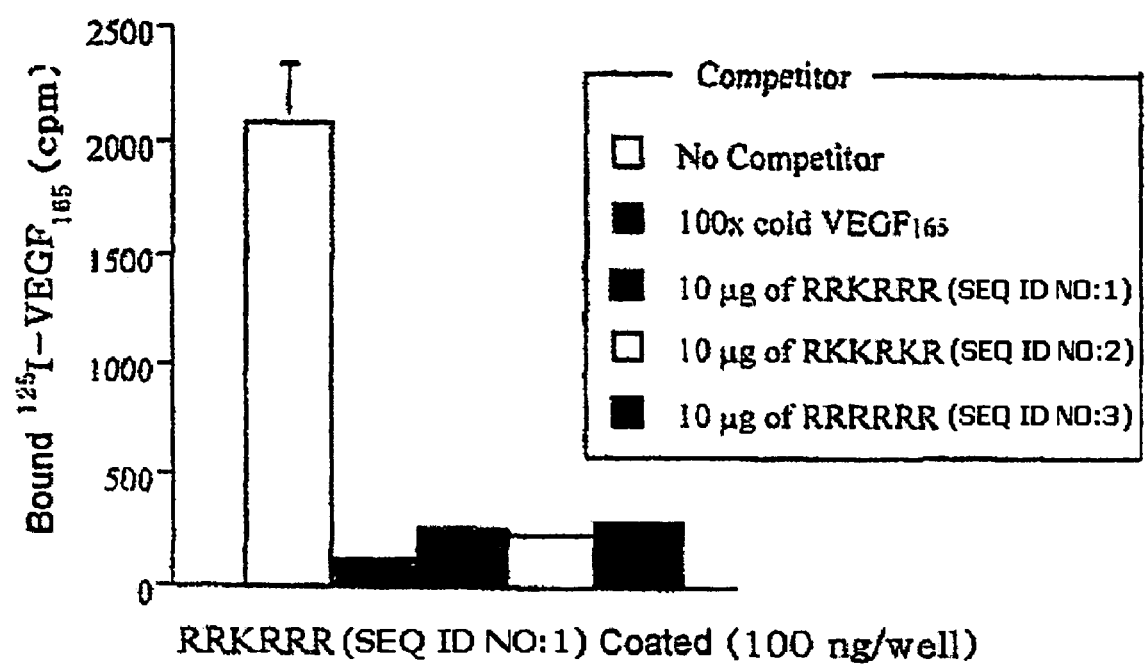
FIG. 8 is a histogram showing radiation quantities measured from $^{125}$I-labeled VEGF associated with a fixed sequence (Sequence 1 (SEQ ID NO: 1)) in the absence of and in the presence of competitors (excess non-labeled VEGF, free Sequences 1 (SEQ ID NO: 1), 2 (SEQ ID NO: 2), and 3 (SEQ ID NO: 3)).

Turning to FIG. 8, there are shown radiation quantities measured from $^{125}$I-labeled VEGF associated with a fixed sequence in the absence of and in the presence of competitors. As seen in the histograms of FIG. 8, the binding of VEGF to a sequence is almost completely prevented in the presence of excess amounts of the free three competitors. These results make it possible to postulate that Sequences 1, 2, and 3 have identical or overlapped binding domains on VEGF.

In order to verify this postulation, Sequence 1 (RRKRRR) was examined for the common binding domain on VEGF because it inhibited the binding of VEGF to its receptors at the highest efficiency. First, appropriate primers were synthesized and used to amplify various cDNAs coding for $VEGF_{165}$, $VEGF_{121}$, $VEFG_{8-121}$, $VEGF_{109}$, and $VEGF_{8-109}$ while a human liver cDNA library (Clontech) served as a template. After being inserted to plasmid pRSET A (Invitrogen), the cDNAs were sequenced. The resulting five pRSET A vectors, each having one of the five cDNAs, were introduced into an expression strain (BL21(DE3)pLysS) containing T7 RNA polymerase. Culturing these transformed cells produced various VEGFs as inclusion bodies which were then separated at a purity of 90% or higher using a method reported previously (Siemeister, G. et al., Biochem. Biophysics. Res. Commun., 222, 249 (1996)). The purified VEGFs were quantified by use of a protein assay reagent (Bio-Rad) and all found to bind to VEGF receptors and exert growth hormone activity on HUVEC. Each of the purified VEGFs was labeled with $^{125}$I (0.5 mCi/S µg of protein) with the aid of IODO-Bead (Pierce). For use, each labeled protein was quantified by ELISA (enzyme-linked immunosorbent assay) using a mouse monoclonal anti-VEGF antibody (R&D systems).

Figure 9:
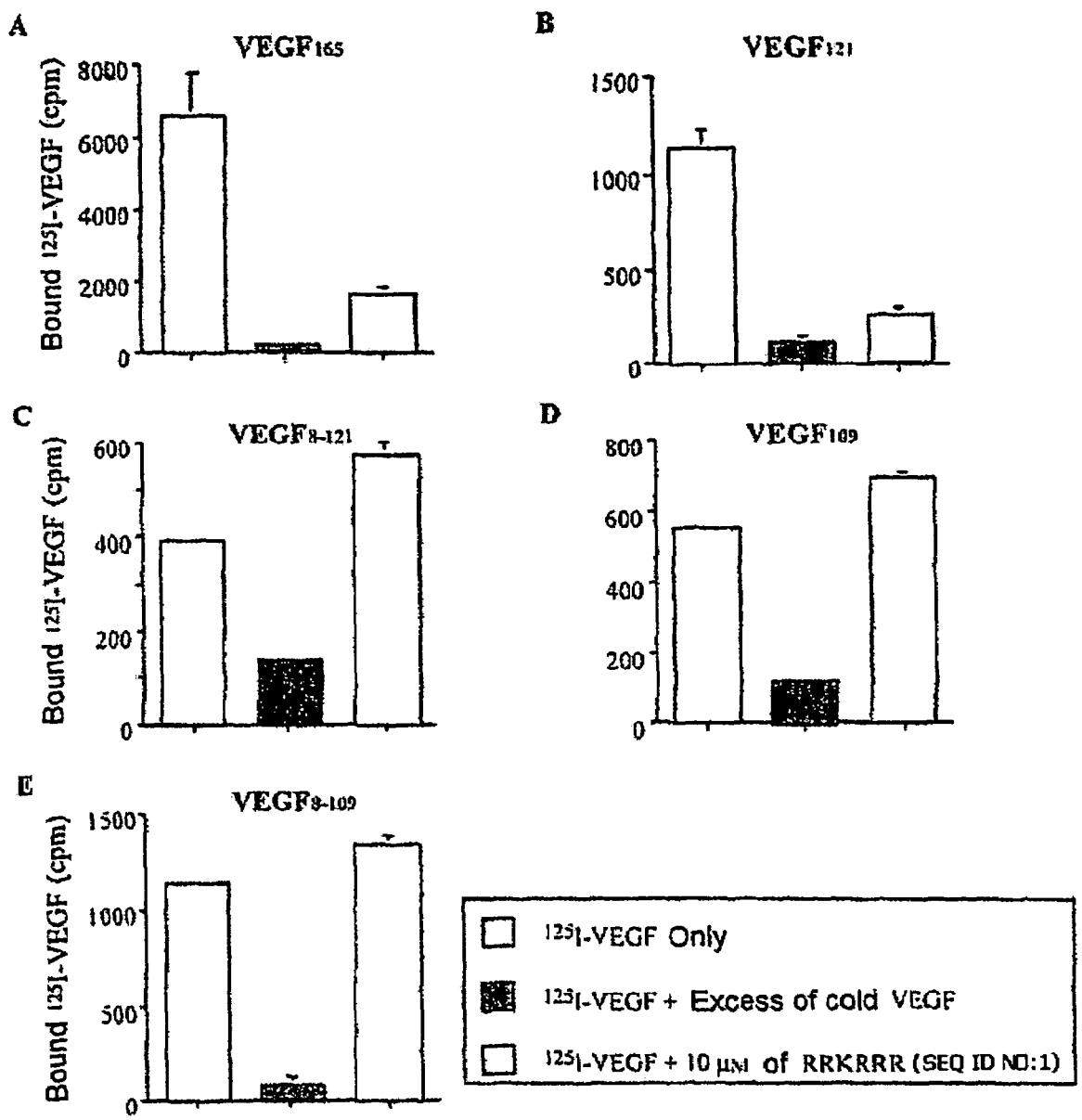
FIG. 9 provides histograms in which the radioactivity measured from $^{125}$I-labeled VEGF associated with fixed Sequence 1 (RRKRRR) (SEQ ID NO: 1) is plotted in the absence of competitors and in the presence of competitors for various VEGF isoforms.

Each peptide was examined for antagonistic activity against VEGF in the same manner as in Example 2. Referring to FIG. 9, the radioactivity measured from $^{125}$I-labeled VEGF associated with fixed Sequence 1 (RRKRRR) (SEQ ID NO: 1) is plotted in the absence of competitors and in the presence of competitors for various VEGF isomers. From the fact that Sequence 1 (RRKRRR) (SEQ ID NO: 1) inhibited not only the binding of labeled $VEGF_{165}$ to its receptors, but the binding of the heparin-binding domain-deficient, labeled $VEGF_{121}$ to its receptors, it can be concluded that the heparin-binding domain of VEGF is independent of the association between the peptides and VEGF. When it was taken into account that the other VEGF isoforms, $VEGF_{8-121}$, $VEGF_{109}$, and $VEGF_{8-109}$, were not inhibited from binding to their receptors by Sequence 1, the amino and the carboxyl ends of the $VEGF_{121}$ were believed to play a key role in binding the peptide to VEGF.

Example 4

Assay for Inhibitory Activity of Peptides Selected Through the Tertiary Search Against VEGF-Stimulated Vascular Endothelial Cell Growth An examination was made in order to determine whether the peptides screened from the peptide combinatorial libraries, Sequence 1, Sequence 2, and Sequence 3, inhibit the VEGF-induced DNA synthesis of HUVEC.

In a gelatin-coated 48-well plate (Nunc) HUVEC were cultured at a density of $10^4$ cells/well at 37° C. for one day, followed by washing the cells three times with serum-free medium 199. After being added with culture media containing VEGF (10 ng/ml, R&D systems) and various concentrations of the screened peptides, the cells were cultured at 37° C. After 24 hours of culturing, the cells were added with [methyl-$^3$H] thymidine (0.5 μCi/well) and cultured for an additional one day. Before quantification of the radioactivity used for the DNA synthesis with the aid of a liquid scintillation counter, the cells were washed with PBS containing 0.1% albumin, treated with 0.4 N NaOH at room temperature for 20 min for cell lysis, and neutralized with 2 N HCl. In order to determine the toxicity of the peptides, HUVEC were examined as in above using excess peptide (100 μM) in the absence of VEGF.

Figure 10A:
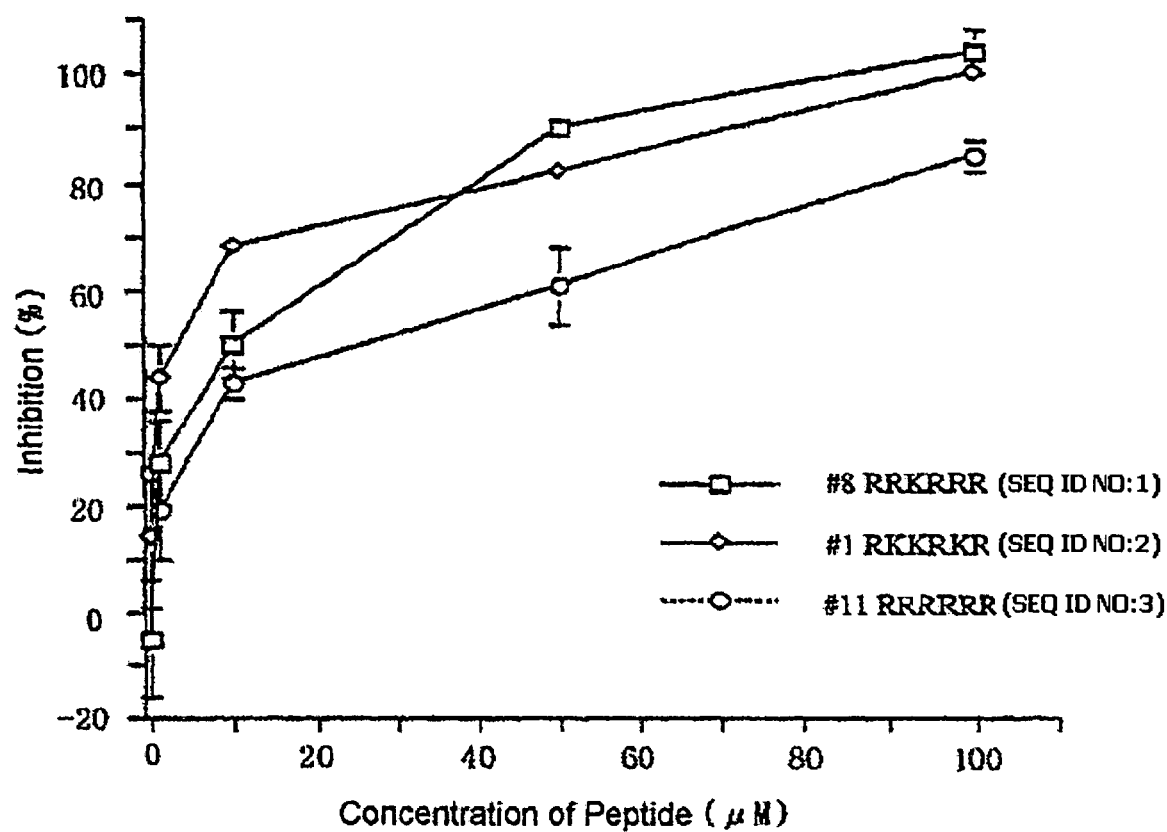
FIG. 10a provides curves showing that the peptides of Sequences 1, 2, and 3 inhibit the VEGF-induced growth of vascular endothelial cells in a dose-dependent pattern.

With reference to FIG. 10a, percent inhibition against DNA synthesis is plotted versus peptide concentration. As seen in FIG. 10a, all of the screened peptides inhibit VEGF-induced DNA synthesis of HUVEC in dose-dependent patterns with $IC_{50}$, values ranging from 10 to 20 μM.

With reference to FIG. 10b, the radioactivity of the thymidine inserted into the genome of HUVEC is measured in the absence of no peptides and in the presence of 100 μM of each of the three peptides. The histograms of FIG. 10b show that the peptides have no direct influence on the growth of HUVEC and therefore lead to the conclusion that the peptides do not exert their inhibitory activity directly to cells.

Based on the results of the above experiments, it was concluded that the three peptides block the binding of VEGF to its receptors to specifically inhibit the growth of endothelial cells induced by VEGF.

Example 5

Assay for Inhibitory Activity of Selected Peptides Against Angiogenesis Induced by VEGF or Human Cancer Cells Secreting VEGF To assay the peptides for anti-angiogenic activity, egg CAM (chorioallantoic membranes) were examined as to whether the peptides inhibit the angiogenesis induced by VEGF.

Fertilized eggs (Pulmuwon, Korea) were incubated at 37° C. under a humidity of 90%. After three days of culturing, the eggs were deprived of about 2 ml of albumin. After four days, eggs were partially deprived of the sheath to make a window with a size of 2×2 cm.

After VEGF (10 ng/egg) was mixed with various amounts of peptides or other samples, 3 μl of each mixture was dropped onto ¼ fraction pieces of thermanox coverslips (Nunc) and dried. The pieces were placed on CAM of 9-day embryonic eggs.

Two days later, the samples were independently observed under anatomical microscopes by two different persons to determine whether new blood vessels are induced by the dropped samples or not. In this regard, the experiment was repeated at least three times using 10 or more eggs per sample and the results are given in Table 5, below.

TABLE 5

| SAMPLE | Angiogenic activity eggs/total eggs | Angiogenic activity(%) | P[a] |
|---|---|---|---|
| WATER | 3/28 | 10.8(1.4)[b] | |
| VEGF (10 ng) | 9/27 | 33.6(3.8) | 0.004 |
| VEGF + RRKRRR (SEQ ID NO: 1) (1 μg) | 4/26 | 15.6(5.1) | 0.245 |
| VEGF + RKKRKR (SEQ ID NO: 2) (1 μg) | 4/26 | 15.6(4.5) | 0.271 |
| VEGF + RRRRRR (SEQ ID NO: 3) (1 μg) | 4/26 | 15.6(5.1) | 0.245 |
| VEGF + KKKKKK (SEQ ID NO: 4) (1 μg) | 8/25 | 32.6(12.2) | 0.038 |
| VEGF + protamine (1 μg) | 5/26 | 18.8(4.1) | 0.128 |
| VEGF + RRRRRR (1 μg) | 4/26 | 15.6(5.1) | 0.245 |
| VEGF + KKKKKK (1 μg) | 8/25 | 32.6(12.2) | 0.038 |
| VEGF + protamine (1 μg) | 5/26 | 18.4(4.1) | 0.128 |

[a]determined by comparing the values between water sample and other samples by use of student's t-test, statistically significant in the case of p < 0.05.
[b]standard deviation As seen in Table 5, VEGF was found to induce angiogenesis at a proportion of 33.6% in the italic model test. This angiogenic activity was effectively reduced to about 15.6% when treating egg samples with the peptides (1 μg/egg), along with VEGF and to about 18.8% when treating egg samples with protamine (50 μg/egg), known as an antiangiogenic factor, along with VEGF. However, a control peptide (KKKKKK, SEQ ID NO: 4), which was not selected in spite of its similar properties to those of the screened peptides, did not show anti-angiogenic activity as it induced angiogenesis at a proportion of about 32.6%.

Figure 11:
FIG. 11 gives photographs of rabbit corneal domes showing the obvious angiogenesis in the test groups treated with VEGF only (A), the anti-angiogenic effect in the test group treated simultaneously with both Sequence 1 RRKRRR (SEQ ID NO: 1) and VEGF (B), and the obvious angiogenesis in the test group treated with the peptide EEFDDA (C) (SEQ ID NO: 5).
Figure 11:
Figure 11:
Figure 12:
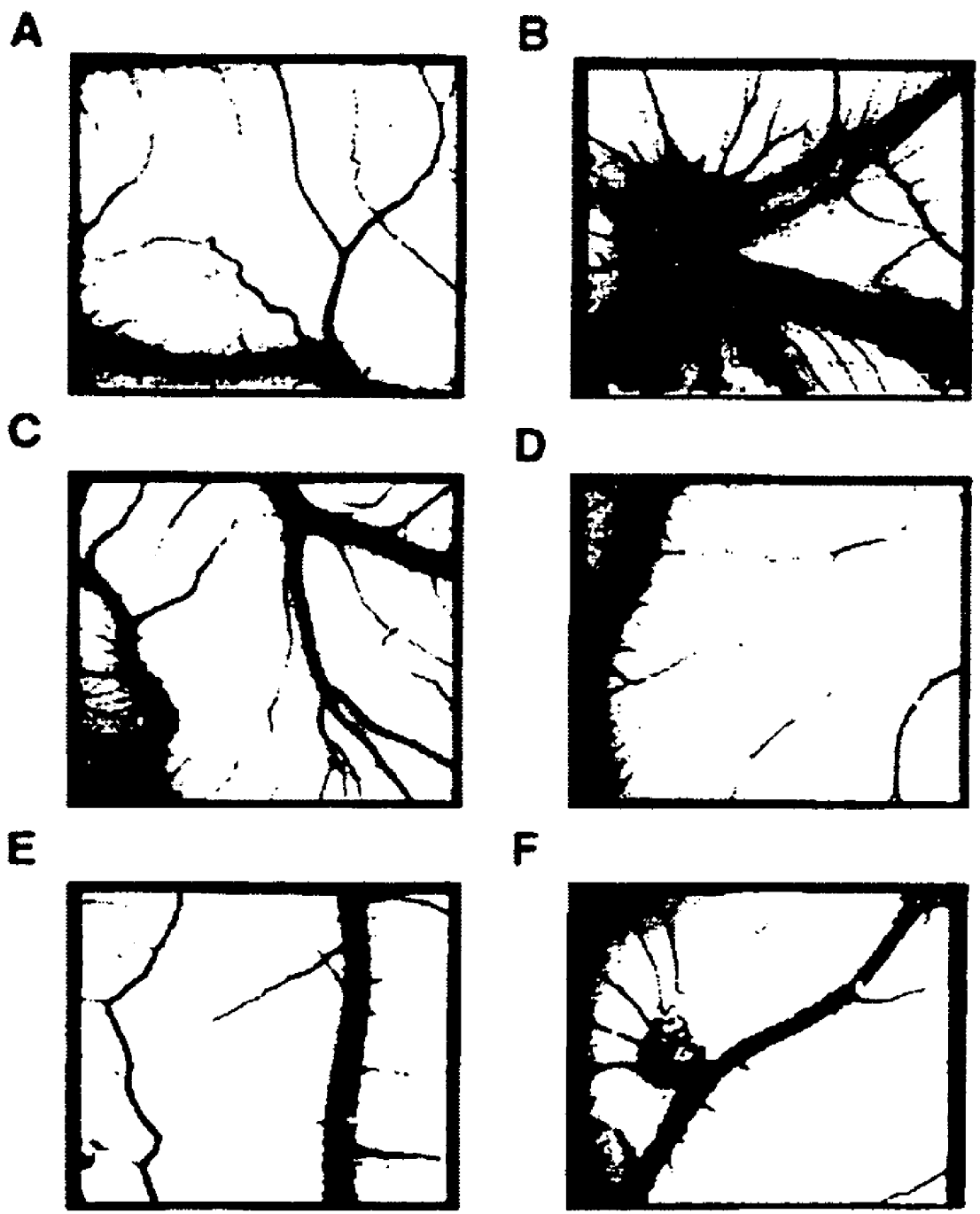
FIG. 12 gives photographs showing the inhibitory effect of Sequences 1, 2, and 3 on the angiogenesis induced by VEGF secreted from human cancer cells.

To confirm the test results obtained from egg CAM, an experiment was performed using rabbit corneal domes for in vivo angiogenesis testing. New Zealand male rabbits weighing 3 kg (SLC, Japan) were subjected to intramuscular ketamine anesthesia (44 mg/kg), followed by dissecting the corneal domes to a length of 3 mm by use of an operating knife (Bard-Parker—#11). VEGF (10 ng, R&D systems) was dropped, alone or in combination with 1 μg of a peptide of an amino acid sequence EEFDDA (SEQ ID NO: 5) or Sequence 1 (RRKRRR) (SEQ ID NO: 1), onto a Thermanox coverslip (Nunc) and dried under germ-free conditions, after which the coverslips were placed on the dissected areas which were then observed for natural healing. 6 rabbits were used per test group within which all animals were observed to show similar results. 16 days after the operation, angiogenesis was obviously observed and photographs were taken of blood vessels newly formed in the corneal dome (Nikon, FS-2, Japan). As seen in photographs of FIG. 11, the control peptide EEFDDA (SEQ ID NO: 5) had no influence on the VEGF-induced angiogenesis in the rabbit corneal dome (FIG. 11C) while the angiogenesis which was obviously observed in the test group treated with VEGF only (FIG. 11A) was completely inhibited in the test group treated simultaneously with both Sequence 1 RRKRRR (SEQ ID NO: 1) and VEGF (FIG. 11B).

The results from the above two experiments and FIG. 10b, taken together, demonstrate that the screened peptides have no direct influence on the growth of vascular endothelial cells, but block the binding of VEGF to its receptors present on the surface of vascular endothelial cells, thereby inhibiting the VEGF-induced angiogenesis in vivo.

An experiment using egg CAM was carried out to confirm the inhibitory activity of the screened peptides against the angiogenesis induced by cancer cells, which secrete VEGF. Fertilized eggs were deprived of albumin and windows were formed on the eggs as in above. 10⁵ cells of HT1080 (human fibrosarcoma) were mixed with 7.5 μg of Type I collagen (rat tail, Beckton Dickinson, USA) within a volume of 5 μl and dropped onto ¼ fraction pieces of Thermanox coverslips to give collagen sponges. After being covered with the collagen sponges, 10-day embryonic egg CAM was incubated at 37° C. for 3 days. Blood vessels induced by the cancer cells were observed and photographed as in above (see Table 6 and FIG. 12).

TABLE 6

| SAMPLE | Angiogenic activity | Angiogenic activity(%) | P³ |
|---|---|---|---|
| No treatment | 5/27 | 18.5(2.1) | |
| Cancer cell | 18/24 | 76.0(8.5) | 0.011 |
| Cancer cell + RRKRRR (SEQ ID NO: 1) (0.1 μg) | 8/22 | 36.0(8.5) | 0.160 |
| Cancer cell + RKKRKR (SEQ ID NO: 2) (0.1 μg) | 10/23 | 43.0(9.9) | 0.141 |
| Cancer cell + RRRRRR (SEQ ID NO: 3) (0.1 μg) | 10/24 | 41.0(7.1) | 0.098 |
| Cancer cell + KKKKKK (SEQ ID NO: 4) (0.1 μg) | 14/22 | 59.0(1.4) | 0.002 |

When having been cultured in egg CAM, human fibro-sarcoma cells, which secrete VEGF, showed a typical "spokewheel" structure (10⁵ cells/egg, 76%). It was observed that when being treated with the screened peptides (100 ng/egg, 36-43%) and the cancer cell, simultaneously, the egg CAM did not undergo angiogenesis. However, the control peptide did not exhibit inhibitory activity with a statistical significance against the cancer cells (100 ng/well, 59%).

Example 6

Assay for Direct Influence of Screened Peptides on Human Fibro-Sarcoma Cell Line The following experiment was carried out to determine whether peptides antagonistic to VEGF have direct influence on the growth of human fibro-sarcoma cells. After being cultured for one day in a 96-well plate (Nunc), the cancer cells were added with DMEM containing various concentrations of the screened peptides and incubated. To the cells remaining alive after 3 days of incubation, 20 μl of tetrazolium dye (Cell Titer 96 Non-Radioactive Proliferation assay kit, Promega) was added, followed by incubation at 37° C. for 4 hours. The formazan produced by the viable cells was dissolved in 0.2 ml of dimethyl sulfoxide (DMSO) quantified by the absorbance at 570 nm. The absorbance attributed to formazan is proportional to living cells.

With reference to FIG. 13, cell viability of human fibroblast sarcoma cells is plotted versus concentrations of peptides. As seen in FIG. 13, all the screened peptides had no direct influence on the growth of human fibro-sarcoma cells.

According to the results obtained from this experiment and Example 5, it is apparent that, without direct influence on the growth of human fibro-sarcoma cells, the screened peptides inhibit the angiogenesis induced by the cancer cells by specifically blocking the binding of VEGF secreted from the cancer cells to its receptors present on the surface of vascular endothelial cells.

Example 7

Assay for Effect of Screened Peptide on Human Colon Carcinoma Cells (HM7)

It was reported that the acquirement of angiogenic ability is crucial to the progression of cancer and indispensable for the continuous growth of cancerous tissues (Hanahan, D. et al., Cell, 86, 353 (1996); Skobe, M., et al., Nature Med., 3, 1222 (1997). Also, the screened peptides were found to effectively inhibit angiogenesis in vivo. With this information, the following experiment was made to determine whether the screened peptides effectively inhibit the growth and metastasis of cancer cells. 5×10⁶ cells of HM7 were added, together with 0.5 μg/μl of an amino acid sequence EEFDDA (SEQ ID NO: 5) or Sequence 1 (RRKRRR) (SEQ ID NO: 1), to a serum-free DMEM and then introduced into male mice which were 4 weeks old (athymic nude mice, BALB/c/nu/nu, Charles River, Japan) by subcutaneous injection. From the next day, a solution of each peptide in PBS (0.5 μg/100 μl/day) was subcutaneously injected to the mice for 15 days. Sizes of the tumors thus formed were periodically measured while tumor volumes were calculated according to the following formula:

Tumor Size=0.5×(Diameter)²×length

In order to conduct an experiment concerning the metastasis of cancer cells to the liver, cancerous cells were transplanted into the spleen. In this regard, after being anesthetized with diethyl ether, 4-week-old male mice (athymic nude mice, BALB/c/nu/nu, Charles River, Japan) underwent flank incision. To the spleen, 100 μl of a mixture containing 10⁶ cells of HM7 (human colon carcinoma cell line) and 0.5 μg/μl of amino acid sequence EEFDDA (SEQ ID NO. 5), KKKKKK (SEQ ID NO: 4), or Sequence 1 (RRKRRR) (SEQ ID NO: 1) was slowly injected, followed by the subcutaneous injection of each peptide for three weeks as in above. Four weeks after the injection, the liver was excised from each mouse and measured for weight and the size and number of metastatic nodules formed. Each test group was composed of 6-7 mice. In a student's t-test, a p value less than 0.05 was regarded as being statistically significant. In the test using tetrazolium dye (cell titer 96 Non-radioactive Proliferation Assay Kit, Promega), each peptide was evaluated to have no influence on the growth of the cancer cells (5×10³ cells/well), so that the possibility that the toxicity of the peptide themselves might inhibit the growth and metastasis of cancer cells could be excluded.

Figure 14:
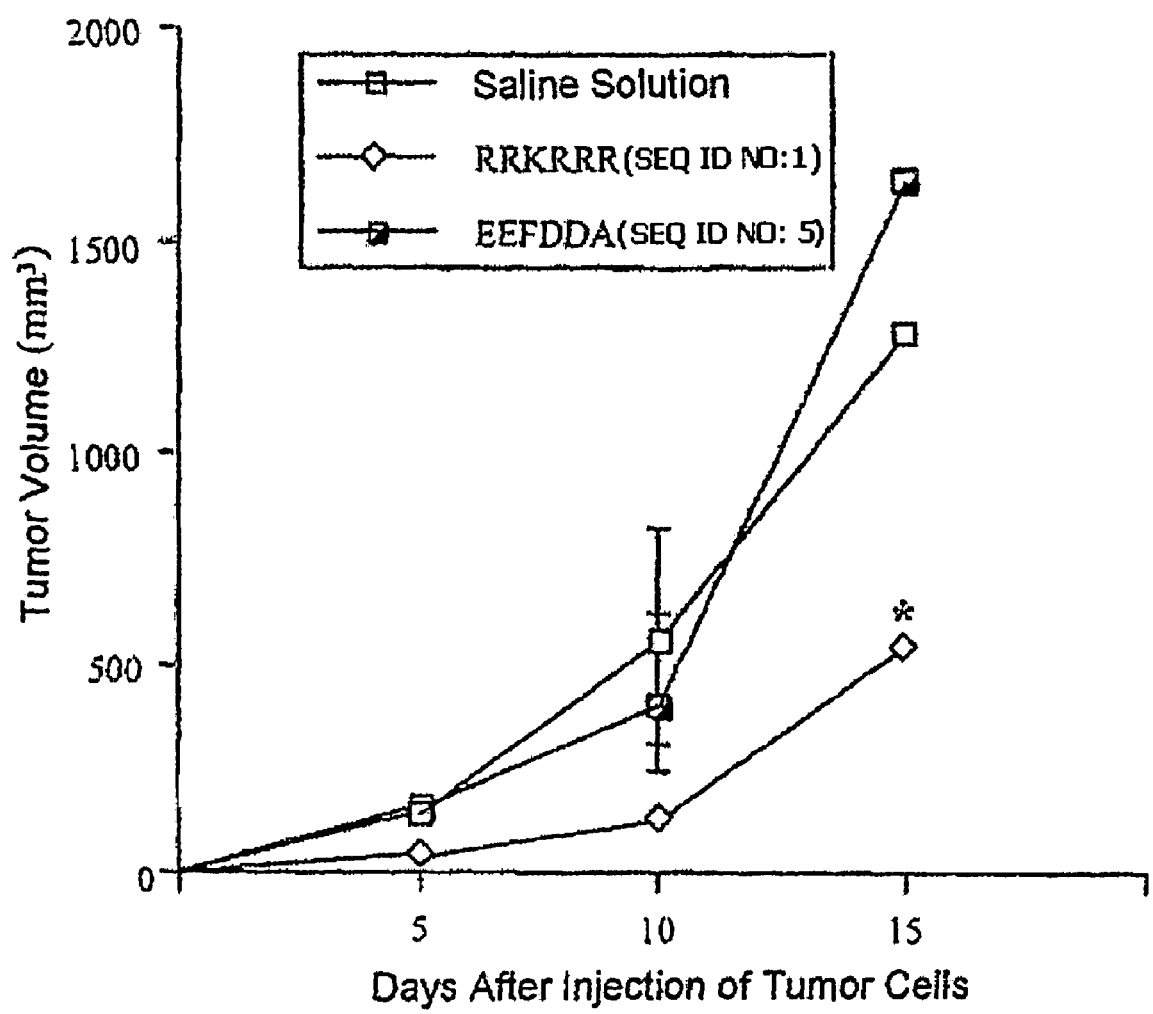
FIG. 14 shows curves in which changes in tumor size are recorded over the time period of injection, demonstrating that the peptide of Sequence 1 (SEQ ID NO: 1) effectively inhibits the growth of human colon carcinoma cells in mice, wherein sequence EEFDDA (SEQ ID NO: 5) exhibited no effects.
Figure 15A:
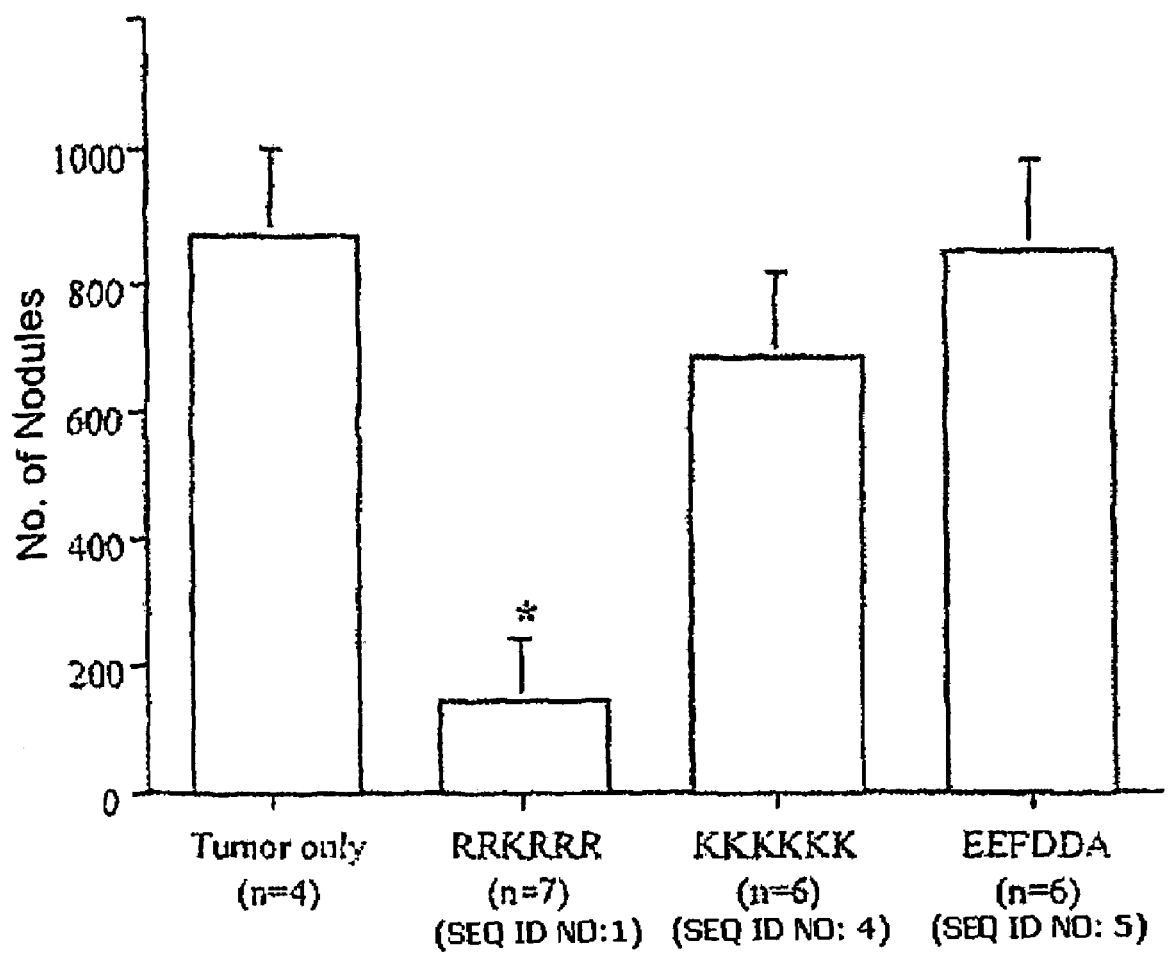
FIG. 15a is a histogram in which the numbers metastatic nodules from spleen to liver are measured after treatment with saline solution and with various peptides (SEQ ID NO: 1, SEQ ID NO: 4, and SEQ ID NO: 5).
Figure 15B:
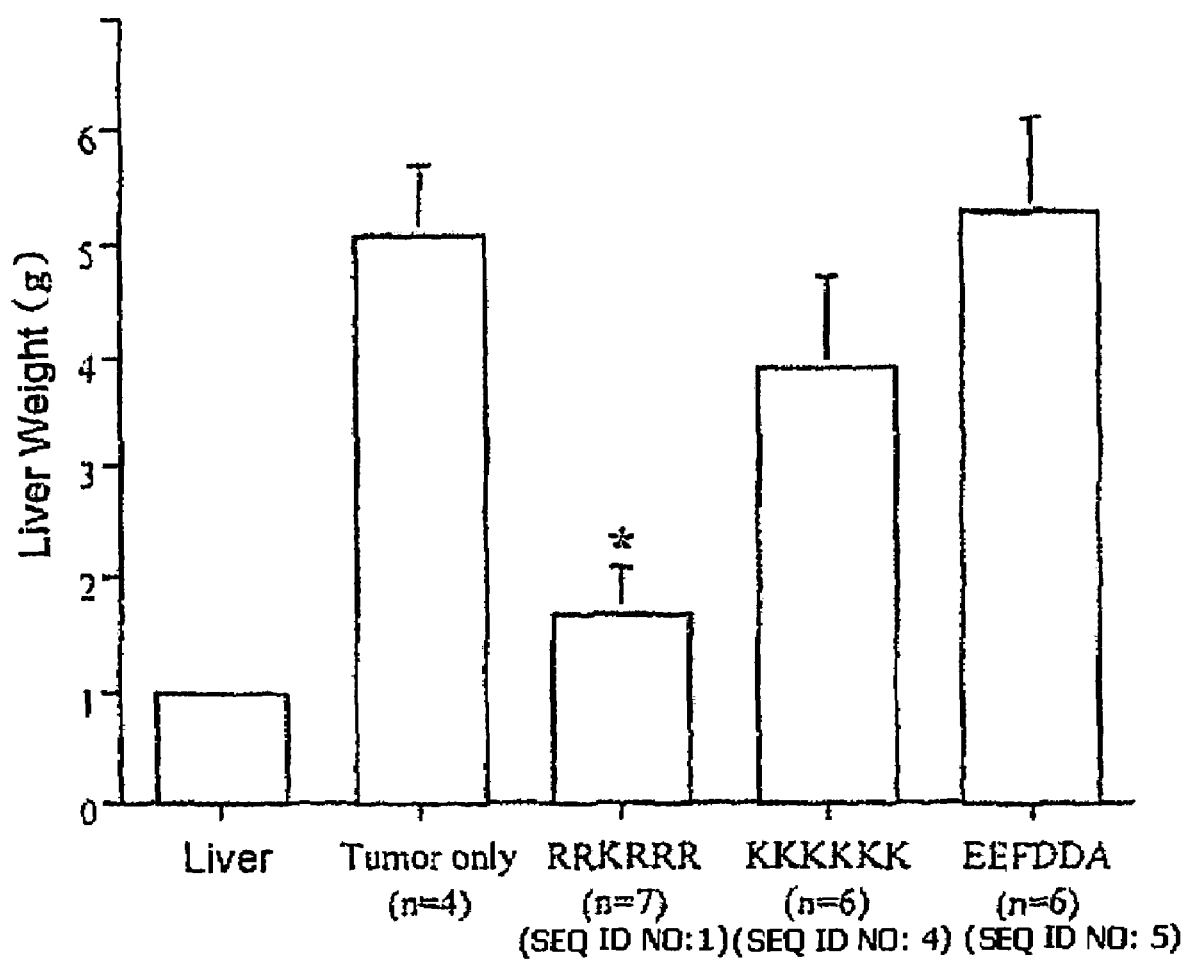
FIG. 15b is a histogram in which the weights of mouse livers to which the human colon carcinoma cells are transferred from the spleen are measured after treatment with various peptides (SEQ ID NO: 1, SEQ ID NO: 4, and SEQ ID NO: 5).

With reference to FIG. 14, changes in tumor size are recorded over the time period of injection. After 15 days of subcutaneous injection, the sequence EEFDDA (SEQ ID NO 5) exhibited no effects whereas the peptide RRKRRR of Sequence 1 (SEQ ID NO: 1) decreased the tumor size by about 28% compared to the control (PBS). Turning to FIG. 15, the numbers of metastatic nodules and liver weights after 14 days of injection are shown according to injected materials. No difference in metastasis of cancer cells could be found between the groups to which tumor was injected alone and together with the sequence EEFDDA (SEQ ID NO: 5). A weak inhibitory activity was observed in the group to which the sequence KKKKKK (SEQ ID NO: 4) was injected (about 80% of the control group to which only PBS was injected). In contrast, high inhibitory effects were found from the test group to which the peptide RRKRRR of Sequence 1 (SEQ ID NO: 1) was injected as the test group was only 16% and 33% of the control group in the number of metastatic nodules and the weight of the liver, respectively. Therefore, it is apparent that the screened peptides shield the signal transduction of VEGF to inhibit the growth and metastasis of malignant tumors.

When the peptides of Sequences 1 (SEQ ID NO: 1), 2 (SEQ ID NO: 2), and 3 (SEQ ID NO: 3) are to be clinically used, parental routes are preferred. They are injected at an effective dose of 0.1-100 μg/kg and preferably at a dose of 0.5-10 μg/kg once a day for 2-3 weeks.

The peptides of Sequences 1 (SEQ ID NO: 1), 2 (SEQ ID NO: 2), and 3 (SEQ ID NO: 3) were tested for acute toxicity through the following experiment.

Example 8

Acute Toxicity Test on Rat Upon Non-Oral Administration

Using specific pathogen-free (SPF) SD rats which were six weeks old, the peptides of Sequences 1, 2, and 3 were tested for acute toxicity. Suspensions of the peptides in 1 ml of PBS were administered at a dose of 1 mg/kg to the rats, which were grouped in twos, by intramuscular injection. After the administration, the animals were observed as to whether they died, which clinical symptoms they showed and how their weights were changed; and serologically and serobiochemically tested. An autopsy was made of the rats with the naked eye to observe whether their abdominal and thoracic organs were damaged. Neither sudden death nor noticeable clinical symptoms were detected in any of the animals administered with the peptides of interest. In addition, no toxicity signs were observed in terms of weight change, serological tests, serobiochemical tests, and corpse 1, examination. Further, italic cytotoxicity tests revealed that the peptides of Sequences 1, 2, and 3 damage neither of endothelial cells, human fibro-sarcoma cells nor human colon carcinoma cells. In consequence, the peptides of Sequences 1, 2, and 3 caused no toxic changes to the rats at a dosage of 1 mg/kg and thus, were found to be safe compounds with a lethal dose (LD50) of at least 1 mg/kg when being administered via a non-oral route.

As described hereinafter, the peptides of the present invention are associated with VEGF to block its binding to receptors present on the surface of vascular endothelial cells, thereby inhibiting the hormonal activity of VEGF, which is related to angiogenesis. Because cancer cells secrete VEGF to generate new blood vessels for their growth and metastasis, the peptides of the present invention are also useful to inhibit the growth and metastasis of cancer cells. Therefore, the peptides of the present invention can be used as therapeutics for angiogenesis-related diseases, including cancer, diabetic retinopathy, rheumatoid arthritis, etc, thanks to superior ability to inhibit the binding of VEGF to its receptors. Additionally, anti-angiogenic therapies for cancer using the peptides of the present invention inhibit the growth of host normal cells (vascular endothelial cells), but not cancer cells themselves, so that they are expected to overcome the problems of conventional therapies for cancer, which are due to the versatility and resistance of cancer cells The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A peptide for inhibiting the activity of vascular endothelial growth factor, consisting of six amino acid residues which comprises arginine at the first, the fourth and the sixth positions from the amino end, one selected from arginine, lysine, and histidine at the second position, and one selected from arginine and lysine at the third and the fifth positions, with the proviso that said peptide does not comprise an amino acid sequence of SEQ ID NO 3, RRRRRR.

2. The peptide as set forth in claim 1, comprising an amino acid sequence of SEQ ID NO: 1.

3. A pharmaceutical composition for the treatment of cancer, comprising the peptide as set forth in claim 1 as a therapeutically effective ingredient.

4. A pharmaceutical composition for the treatment of angiogenesis-related diseases, comprising the peptide as set forth in claim 1 as a therapeutically effective ingredient.

* * * * *

UNITED STATES PATENT AND TRADEMARK OFFICE
CERTIFICATE OF CORRECTION

| | | |
|---|---|---|
| PATENT NO. | : 7,291,601 B1 | Page 1 of 1 |
| APPLICATION NO. | : 09/913956 | |
| DATED | : November 6, 2007 | |
| INVENTOR(S) | : Chi Bom Chae et al. | |

It is certified that error appears in the above-identified patent and that said Letters Patent is hereby corrected as shown below:

Column 19, Line 41, after "NO" insert --:--.

Signed and Sealed this

Tenth Day of June, 2008

JON W. DUDAS
*Director of the United States Patent and Trademark Office*